(12) United States Patent
Natrajan et al.

(10) Patent No.: US 11,332,445 B2
(45) Date of Patent: May 17, 2022

(54) HYDROPHILIC HIGH QUANTUM YIELD ACRIDINIUM ESTERS WITH IMPROVED STABILITY AND FAST LIGHT EMISSION

(71) Applicant: Siemens Healthcare Diagnostics Inc., Tarrytown, NY (US)

(72) Inventors: Anand Natrajan, Manchester, NH (US); David Sharpe, Foxborough, MA (US); Qingping Jiang, East Walpole, MA (US); David Wen, Northborough, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/801,354

(22) Filed: Feb. 26, 2020

(65) Prior Publication Data

US 2020/0190037 A1 Jun. 18, 2020

Related U.S. Application Data

(62) Division of application No. 14/901,009, filed as application No. PCT/US2014/045505 on Jul. 4, 2014, now abandoned.

(Continued)

(51) Int. Cl.
| | |
|---|---|
| *G01N 33/543* | (2006.01) |
| *C07D 219/06* | (2006.01) |
| *G01N 21/76* | (2006.01) |
| *F21K 2/06* | (2006.01) |
| *G01N 33/58* | (2006.01) |
| *C09K 11/07* | (2006.01) |

(52) U.S. Cl.
CPC ............ *C07D 219/06* (2013.01); *C09K 11/07* (2013.01); *F21K 2/06* (2013.01); *G01N 21/76* (2013.01); *G01N 33/543* (2013.01); *G01N 33/582* (2013.01)

(58) Field of Classification Search
CPC ......... C07D 219/06; C09K 11/07; F21K 2/06; G01N 21/76; G01N 33/582; G01N 33/543
USPC ........................................ 546/103; 435/7.92
See application file for complete search history.

(56) References Cited

U.S. PATENT DOCUMENTS

| | | | |
|---|---|---|---|
| 7,309,615 B2 | 12/2007 | Natrajan et al. | |
| 7,785,904 B2 | 8/2010 | Natrajan et al. | |
| 8,778,624 B2 * | 7/2014 | Natrajan ............... | C07D 219/14 435/7.92 |

FOREIGN PATENT DOCUMENTS

| | | |
|---|---|---|
| CN | 101918367 | 12/2010 |
| CN | 102762539 | 10/2012 |

(Continued)

OTHER PUBLICATIONS

Anand Natrajan et al: "Chemiluminescence from alkoxy-substituted acridinium dimethylphenyl ester labels", Organic & Biomolecular Chemistry, vol. 10, No. 17, pp. 3432-3447, XP055314617, GB ISSN: 1477-0520, DOI: 10.1039/c2ob00022a / Jan. 1, 2012.

(Continued)

*Primary Examiner* — Taylor V Oh

(57) ABSTRACT

Hydrophilic, high quantum yield, chemiluminescent acridinium compounds with increased light output, improved stability, fast light emission and decreased non specific binding are disclosed. The chemiluminescent acridinium (Continued)

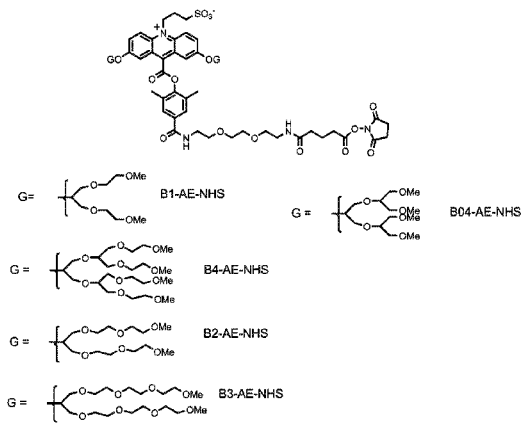

Structures of B-AEs with electrophilic functional groups.

esters possess hydrophilic, branched, electron-donating functional groups at the C2 and/or C7 positions of the acridinium nucleus.

11 Claims, 3 Drawing Sheets

Related U.S. Application Data

(60) Provisional application No. 61/843,528, filed on Jul. 8, 2013.

(56) References Cited

FOREIGN PATENT DOCUMENTS

| | | |
|---|---|---|
| JP | 2010506857 | 3/2010 |
| JP | 2011503235 | 1/2011 |
| JP | 2013510934 | 3/2013 |
| WO | 2006130736 | 12/2006 |
| WO | 2008067055 | 6/2008 |
| WO | WO-2008067055 A2 * | 6/2008 ........... C07D 219/04 |
| WO | 2009067417 | 5/2009 |
| WO | WO-2009067417 A1 * | 5/2009 ........... C07D 219/04 |
| WO | 2011060228 | 5/2011 |
| WO | WO-2011060228 A1 * | 5/2011 ........... C07D 219/04 |

OTHER PUBLICATIONS

Natrajan A et al.:", Enhanced immunoassay sensitivity using chemiluminescent acridinium esters with increased light output", Analytical Biochemistry, Elsevier, Amsterdam, NL, vol. 406, No. 2, pp. 204-213, XP027259644, ISSN: 0003-2697/15.11.2010.

Anand Natrajan et al: "Facile N-alkylation of acridine esters with 1,3-propane sultone in ionic liquids", Green Chemistry, vol. 13, No. 4, pp. 913-921, XP055185019, ISSN: 1463-9262, DOI: 10.1039/c0gc00758g / Jan. 1, 2011.

Search Report and Written Opinion for PCT Application No. PCT/US14/45505 dated Oct. 15, 2014, 6 pp.

* cited by examiner

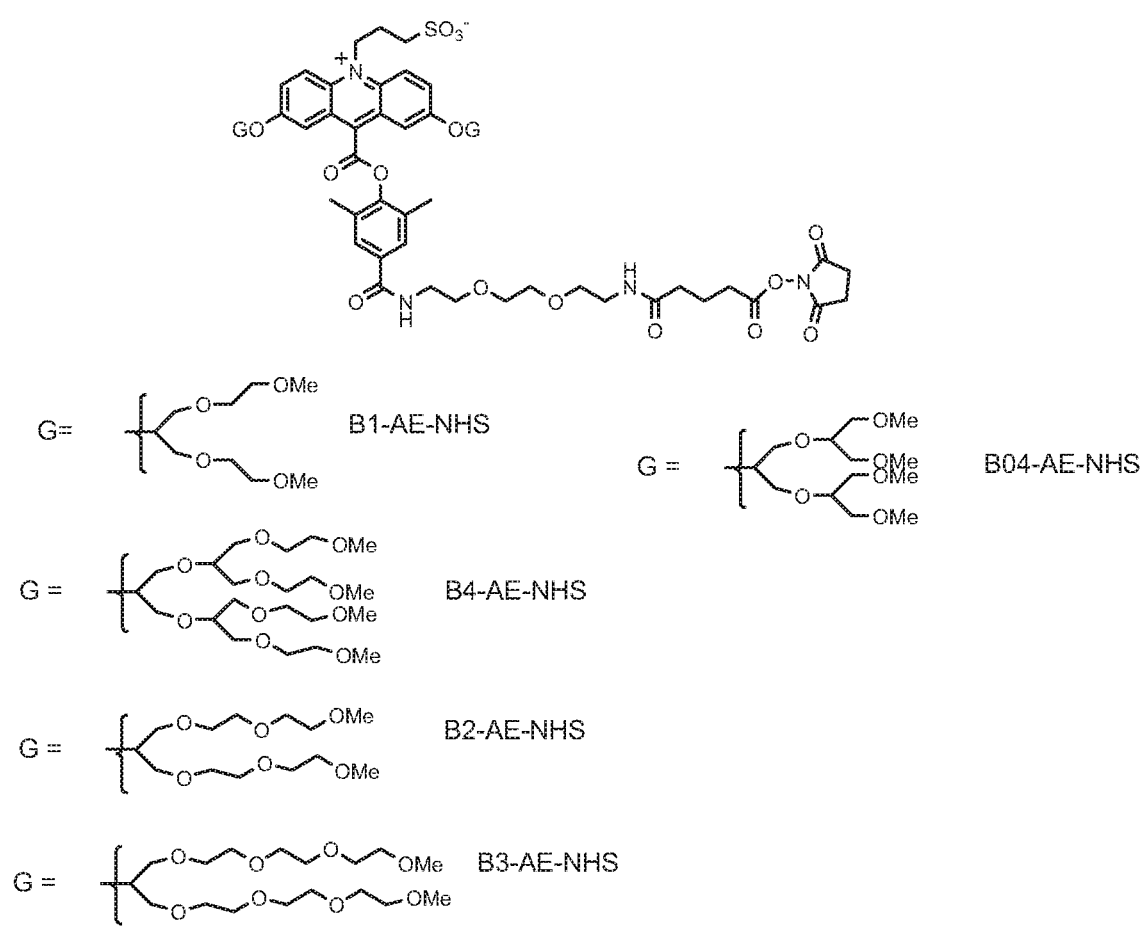
Figure 1. Structures of B-AEs with electrophilic functional groups.

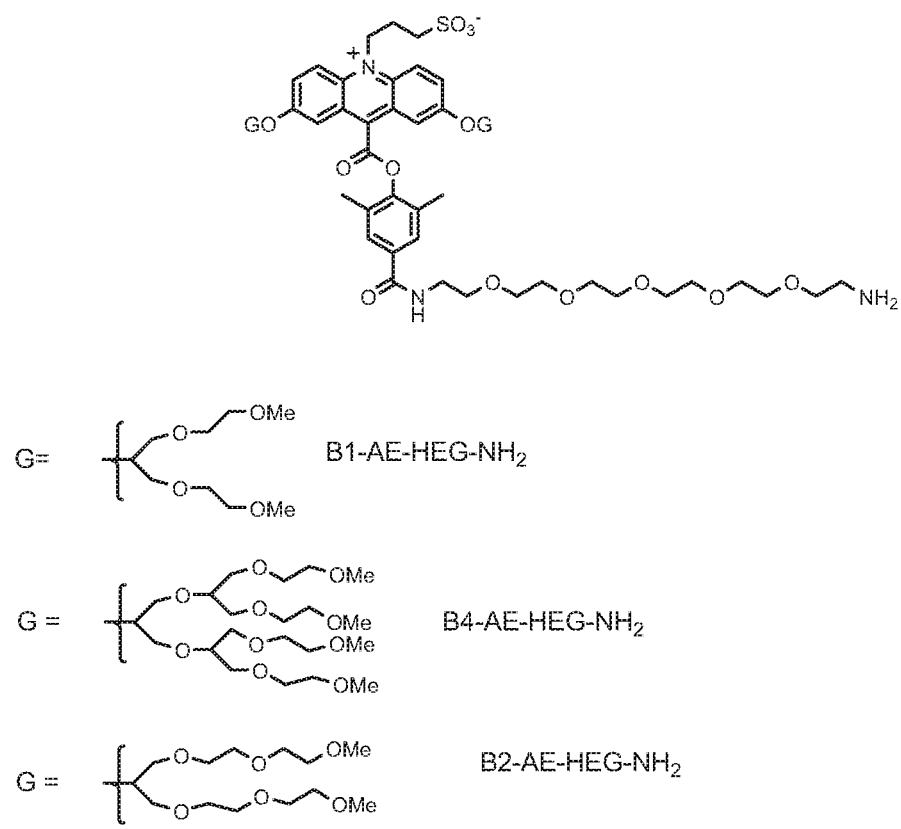
Figure 2. Structures of B-AEs with nucleophilic functional groups.

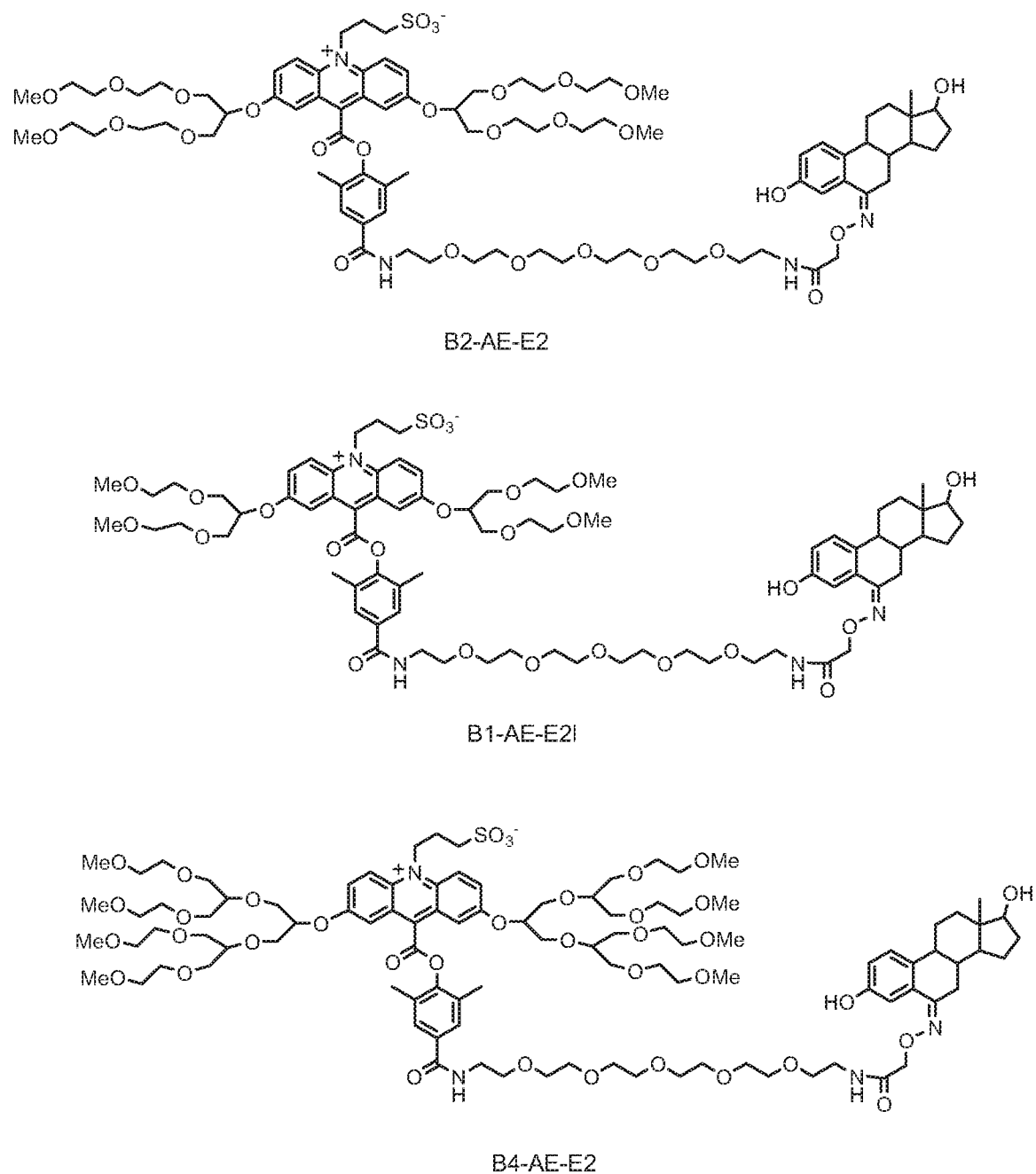
Figure 3. Structures of B-AE-E2 conjugates.

HYDROPHILIC HIGH QUANTUM YIELD ACRIDINIUM ESTERS WITH IMPROVED STABILITY AND FAST LIGHT EMISSION

1. CROSS-REFERENCE TO RELATED APPLICATIONS

This application claims priority to U.S. Provisional Application Ser. No. 61/843,528 filed Jul. 8, 2013, which is incorporated herein by reference in its entirety.

2. FIELD OF THE INVENTION

The present invention relates to hydrophilic, high quantum yield, chemiluminescent acridinium compounds with increased light output, improved stability, fast light emission and low non-specific binding. These compounds because of their enhanced quantum yield and hydrophilic nature, are useful in improving assay sensitivity. The improved stability of these compounds is useful for extending the shelf life of reagents using these compounds as well as for minimizing variation in assay performance with time. Their increased emission kinetics also permits faster light measurements in assays especially in automated analyzers.

3. BACKGROUND OF THE INVENTION

Chemiluminescent acridinium esters (AEs) are extremely useful labels that have been used extensively in immunoassays and nucleic acid assays. A review by Pringle, M. J. *Journal of Clinical Ligand Assay* vol. 22, pp. 105-122 (1999) summarizes past and current developments in this class of chemiluminescent compounds.

McCapra, F. et al. in *Tetrahedron Lett.* vol. 43, pp. 3167-3172 (1964) and Rahut et al. in *J. Org. Chem* vol. 301, pp. 3587-3592. (1965) disclosed that chemiluminescence from the esters of acridinium salts can be triggered by alkaline peroxide. Since these seminal studies, interest in acridinium compounds has increased because of their utility as labels. The application of the acridinium ester 9-carboxyphenyl-N-methylacridinium bromide in an immunoassay was disclosed by Simpson, J. S. A. et al., *Nature*, vol. 279, pp. 646-647 (1979). However, this acridinium ester is quite unstable, thereby limiting its commercial utility. This instability arises from hydrolysis of the 9-carboxyphenyl ester linkage between the phenol and the acridinium ring.

Different strategies for increasing the stability of acridinium compounds have been described. Law et al., *Journal of Bioluminescence and Chemiluminescence*, vol. 4, pp. 88-89 (1989), introduced two methyl groups to flank the acridinium ester moiety to stabilize this linkage. The resulting sterically stabilized acridinium ester, DMAE-NHS [2',6'-dimethyl-4'-(N-succinimidyloxycarbonyl)phenyl 10-methylacridinium-9-carboxylate] was found to have the same light output as an acridinium ester lacking the two methyl groups. The stability of the former compound when conjugated to an immunoglobulin was vastly superior and showed no loss of chemiluminescent activity even after one week at 37° C. at pH 7. In contrast, the unsubstituted acridinium ester only retained 10% of its activity when subjected to the same treatment. U.S. Pat. Nos. 4,918,192 and 5,110.932 describe DMAE and its applications.

U.S. Pat. No. 5,656,426 to Law et al. discloses a hydrophilic version of DMAE termed NSP-DMAE-NHS ester where the N-methyl group has been replaced with an N-sulfopropyl (NSP) group. The structures of these two compounds and the numbering system of the acridinium ring are illustrated below.

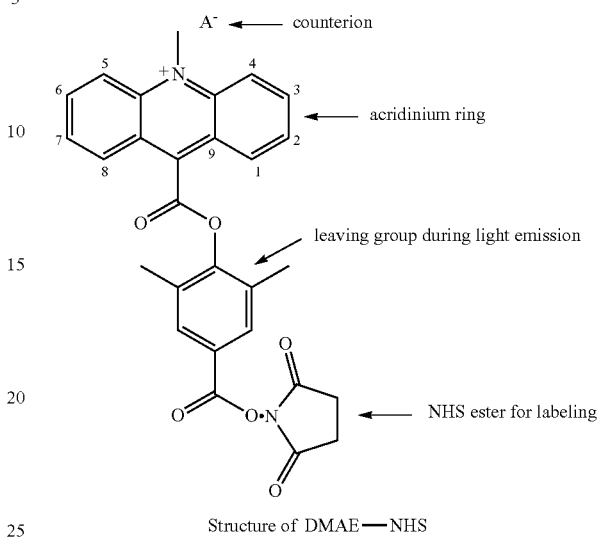

Structure of DMAE—NHS

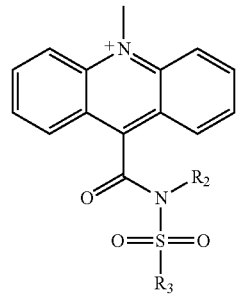

General structure of an acridinium sulfonamide (R2 and R3 are alkyl or aryl groups)

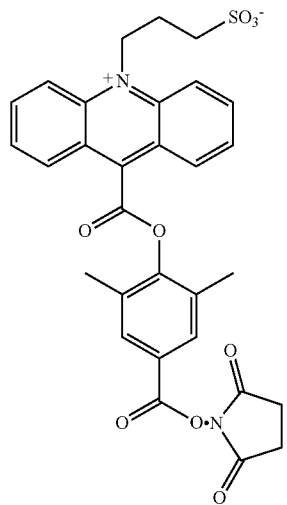

Structure of NSP—DMAE—NHS

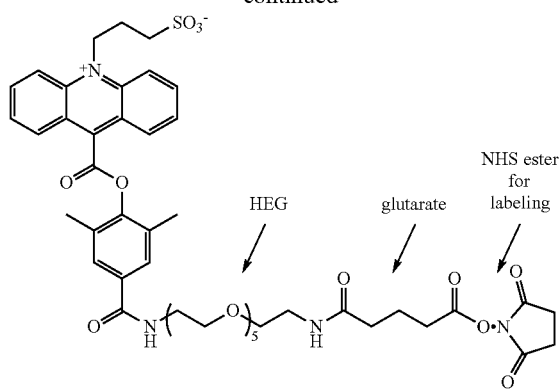

Structure of NSP—DMAE—HEG-Glutarate-NHS

Natrajan et al. in U.S. Pat. No. 6,664,043 B2 disclosed NSP-DMAE derivatives with hydrophilic modifiers attached to the phenol. The structure of one such compound, NSP-DMAE-HEG-Glutarate-NHS, (abbreviated as HEG-AE) is illustrated in the above. In this compound a diamino hexa (ethylene) glycol (diamino-HEG) moiety is attached to the phenol to increase the aqueous solubility of the acridinium ester. A glutarate moiety was appended to the end of HEG and was converted to the NHS ester to enable labeling of various molecules.

A different class of stable chemiluminescent acridinium compounds has been described by Kinkel et al., *Journal of Bioluminescence and Chemiluminescence* vol. 4, pp. 136-139 (1989) and Mattingly, *Journal of Bioluminescence and Chemiluminescence* vol. 6, pp. 107-114 (1991) and U.S. Pat. No. 5,468,646. In this class of compounds, the phenolic ester linkage is replaced by a sulfonamide moiety, which is reported to impart hydrolytic stability without compromising the light output. In acridinium esters, the phenol is the 'leaving group' whereas in acridinium sulfonamides, the sulfonamide is the 'leaving group' during the chemiluminescent reaction with alkaline peroxide.

Light emission from acridinium compounds is normally triggered by alkaline peroxide. The overall light output, which can also be referred to as the chemiluminescence quantum yield, is a combination of the efficiencies of the chemical reaction leading to the formation of the excited-state acridone and the latter's fluorescence quantum yield.

Recently, Natrajan et al. in U.S. Pat. No. 7,309,615 B2, the disclosure of which is hereby incorporated by reference herein, described hydrophilic, high quantum yield acridinium compounds containing hydrophilic alkoxy groups (OR*) at C2 and/or C7 of the acridinium ring, wherein R* is a group comprising a sulfopropyl moiety or ethylene glycol moieties or a combination thereof. The enhanced light output from such compounds and their hydrophilic nature made them useful for improving the sensitivity of immunoassays. The structure of one such compound, NSP-2,7-(OMHEG)$_2$-DMAE-AC-NHS (abbreviated as HQYAE), is illustrated below.

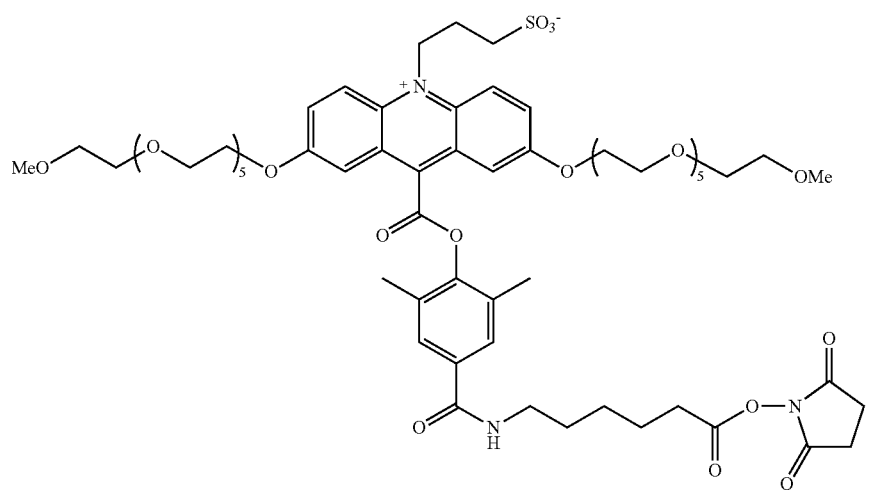

Structure or NSP-2,7-(OMHEG)$_2$-DMAE-AC-NHS

4. SUMMARY OF INVENTION

It has surprisingly been found that hydrophilic, high quantum yield, chemiluminescent acridinium esters possessing electron-donating functional groups of the form —OG at C2 and/or C7 of the acridinium ring, where G represents a branched hydrophilic substituent, provide increased light output, improved stability, fast light emission and/or low non-specific binding in assays.

In one aspect of the invention, hydrophilic, high quantum yield acridinium esters are provided having the structure of formula (I):

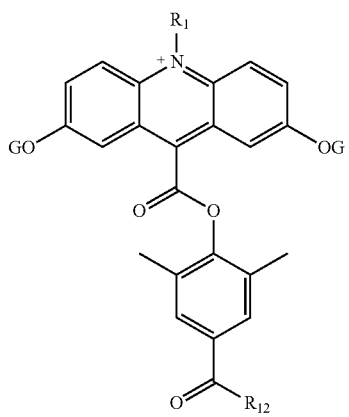
(I)

wherein, $R_1$ is a methyl or sulfopropyl group; G is a branched group independently selected at each occurrence from:

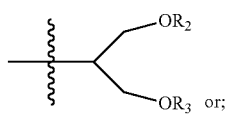
(i)

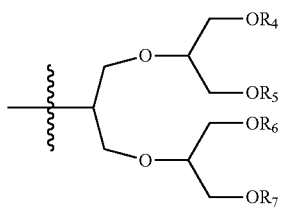
(ii)

where $R_2$, $R_3$, $R_4$, $R_5$, $R_6$ and $R_7$ are independently at each occurrence a methyl group or a group —$(CH_2CH_2O)_nCH_3$, where n is an integer from 1 to 5; and $R_{12}$ is an electrophilic or nucleophilic group for conjugating the acridinium compound to an analyte, an analyte analog, or a binding molecule for an analyte.

In some embodiments according to formula (I), G will be, at one or both occurrences, a group:

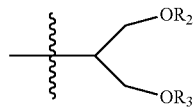

where $R_2$ and $R_3$ are independently at each occurrence a methyl group or a group
—$(CH_2CH_2O)_nCH_3$, where n is an integer from 1 to 5; and in particular, G may be a group:

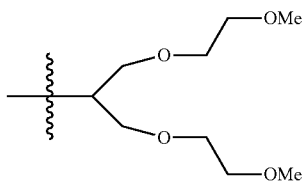 [SMILES: *C(COCCOC)COCCOC]

at one or both occurrences; or in another embodiment G may be a group:

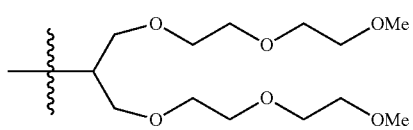 [SMILES: *C(COCCOCCOC)COCCOCCOC]

at one or both occurrences. In a related embodiment, G is a group:

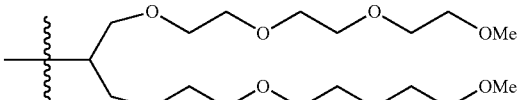

at one or both occurrences.

In other embodiments according to formula (I), G represents, at one or both occurrences, a group:

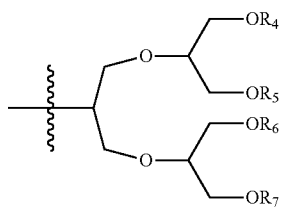

where $R_4$, $R_5$, $R_6$ and $R_7$ are independently at each occurrence a methyl group or a group —$(CH_2CH_2O)_nCH_3$, where n is an integer from 1 to 5. In one variant according to this embodiment, $R_4$-$R_7$ may represent methyl groups, such that G is a group:

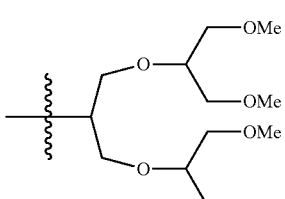

at one or both occurrences.

In one embodiment according to formula (I), G is a group:

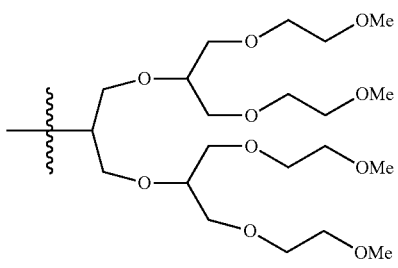 [SMILES: *C(COC(COCCOC)COCCOC)COC(COCCOC)COCCOC]

at one or both occurrences.

In the acridinium esters according to formula (I), $R_{12}$ may be selected, for example, from the group consisting of:
(1) —OH;
(2) —O—N-succinimidyl;
(3) —NH—(CH$_2$)$_5$—C(O)—O—N-succinimidyl;
(4) —NH—(CH$_2$)$_5$—COOH;
(5) —NH—(C$_2$H$_4$O)$_n$—C$_2$H$_4$NH—C(O)—(CH$_2$)$_3$—C(O)—O—N-succinimidyl wherein n=1 to 5;
(6) —NH—(C$_2$H$_4$O)$_n$—C$_2$H$_4$NH—C(O)—(CH$_2$)$_3$—COOH, wherein n=1 to 5;
(7) —NH—(C$_2$H$_4$O)$_n$—C$_2$H$_4$NH$_2$, wherein n=1 to 5; and
(8) —NH—R—NHR, wherein R is independently hydrogen, alkyl, alkenyl, alkynyl, or aralkyl; wherein R optionally comprises up to 20 heteroatoms.

In various illustrative embodiments, $R_{12}$ will be —OH, or $R_{12}$ will be a group:
—NH—(C$_2$H$_4$O)$_n$—C$_2$H$_4$NH$_2$, wherein n=1 to 5,
or $R_{12}$ will be a group:
—NH—(C$_2$H$_4$O)$_n$—C$_2$H$_4$NH—C(O)—(CH$_2$)$_3$—C(O)—O—R″, where n=1 to 5; and where R″ is hydrogen or —N-succinimidyl.

One acridinium ester according to formula (I) has the following structure:

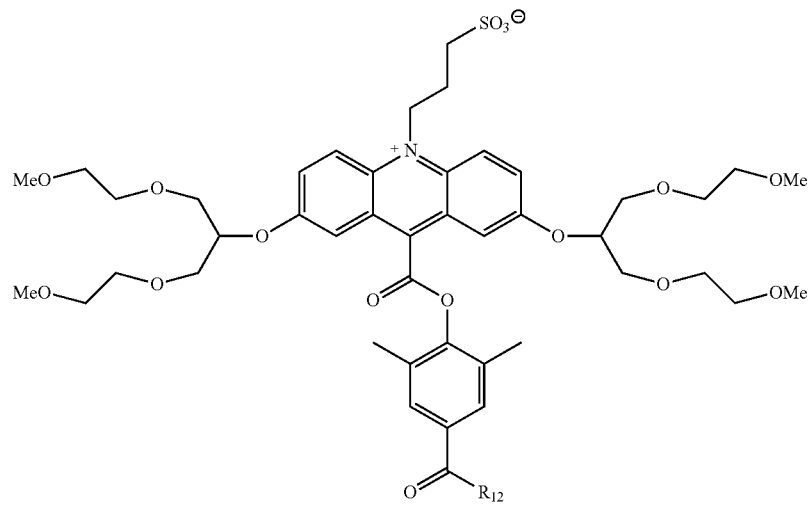

where $R_{12}$ is an electrophilic or nucleophilic group for conjugating the acridinium compound to an analyte, an analyte analog, or a binding molecule for an analyte.

Another acridinium ester according to formula (I) has the following structure:

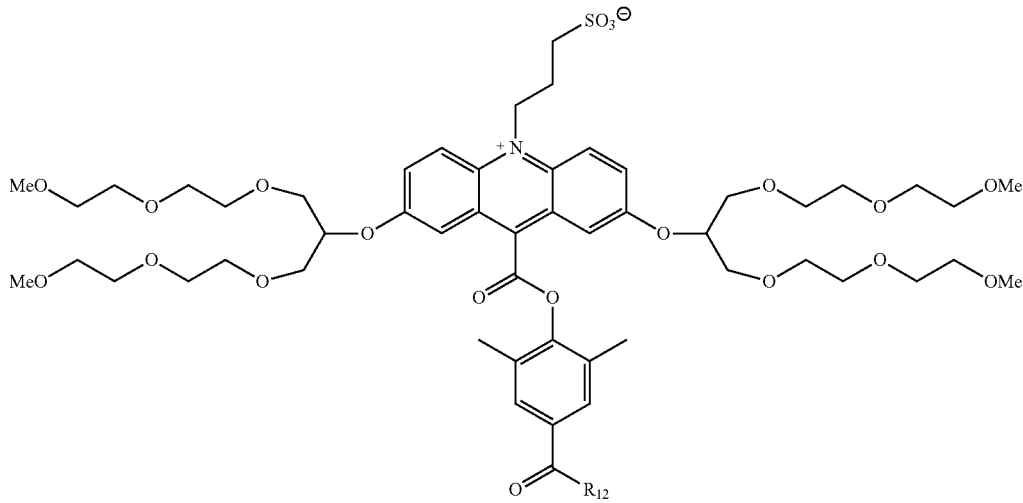

where $R_{12}$ is an electrophilic or nucleophilic group for conjugating the acridinium compound to an analyte, an analyte analog, or a binding molecule for an analyte.

Yet another acridinium ester according to formula (I) has the following structure:

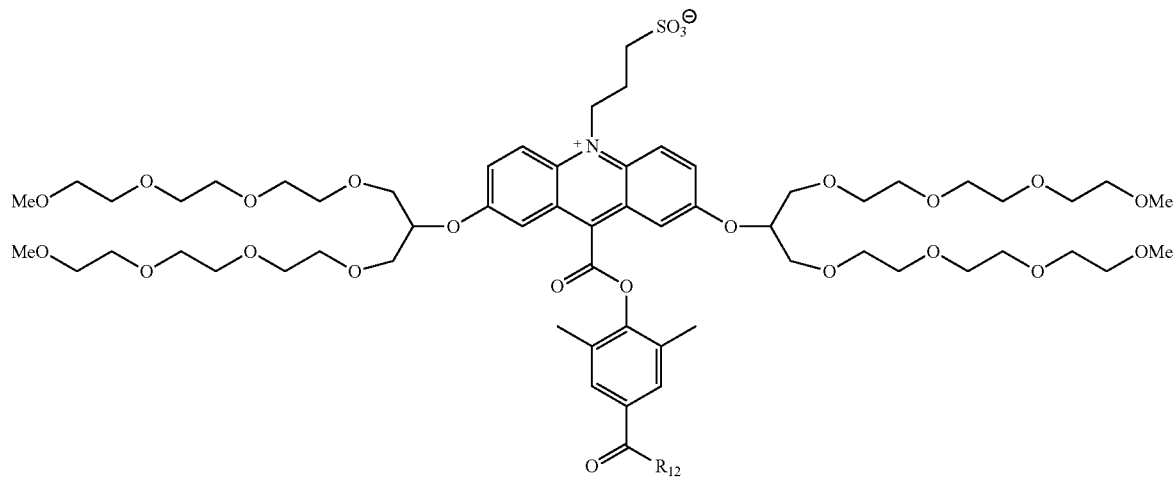

where $R_{12}$ is an electrophilic or nucleophilic group for conjugating the acridinium compound to an analyte, an analyte analog, or a binding molecule for an analyte.

Another acridinium ester according to formula (I) has the following structure:

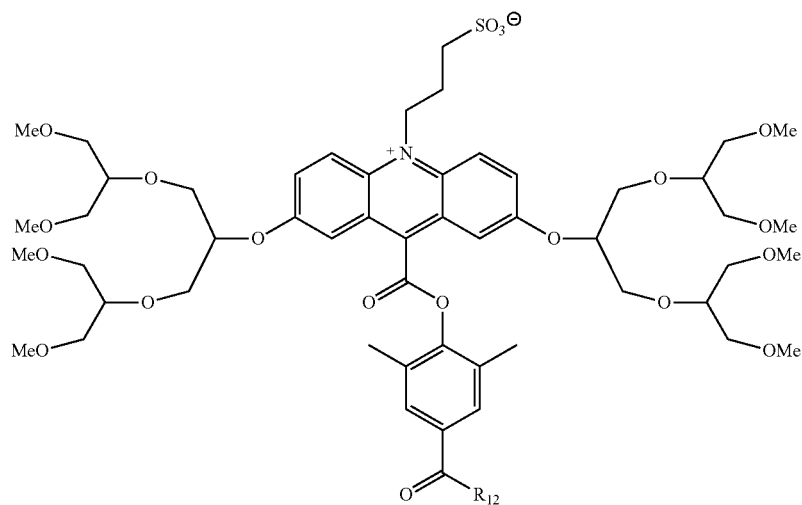

where $R_{12}$ is an electrophilic or nucleophilic group for conjugating the acridinium compound to an analyte, an analyte analog, or a binding molecule for an analyte.

Still another acridinium ester according to formula (I) has the following structure:

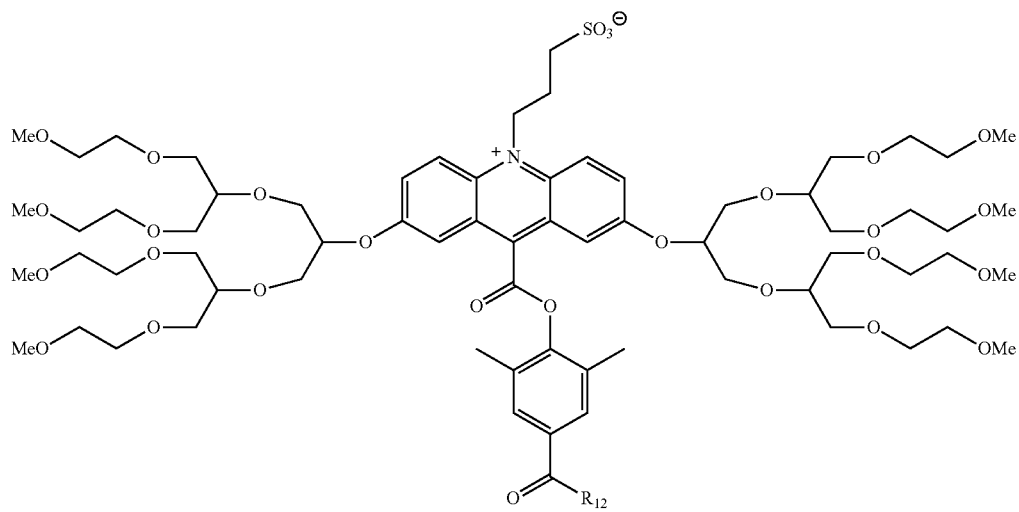

where $R_{12}$ is an electrophilic or nucleophilic group for conjugating the acridinium compound to an analyte, an analyte analog, or a binding molecule for an analyte.

In one exemplary embodiment of the acridinium esters according to formula (I), $R_{12}$ represents —OH.

In another aspect of the invention, an assay for the detection or quantification of an analyte is provided comprising the steps of: (a) providing a conjugate comprising: (i) a binding molecule specific for an analyte; and (ii) a hydrophilic, high quantum yield and fast light emitting acridinium ester according to formula (I); (b) providing a solid support having immobilized thereon a second binding molecule specific for the analyte; (c) mixing the conjugate, the solid phase and a sample suspected of containing the analyte to form a binding complex; (d) separating the binding complex captured on the solid support; (e) triggering chemiluminescence of the binding complex from step (d) by adding chemiluminescence triggering reagents; (f) measuring the amount of light emission with a luminometer; and (g) detecting the presence or calculating the concentration of the analyte by comparing the amount of light emitted from the reaction mixture with a standard dose response curve which relates the amount of light emitted to a known concentration of the analyte.

In a related aspect, an assay for the detection or quantification of an analyte is provided comprising the steps of: (a) providing a conjugate of an analyte with a hydrophilic, high quantum yield and fast light emitting acridinium ester according to formula (I); (b) providing a solid support immobilized with a binding molecule specific for the analyte; (c) mixing the conjugate, solid support and a sample suspected of containing the analyte to form a binding complex; (d) separating the binding complex captured on the solid support; (e) triggering the chemiluminescence of the binding complex from step (d) by adding chemiluminescence triggering reagents; (f) measuring the amount of light with an luminometer; and (g) detecting the presence or calculating the concentration of the analyte by comparing the amount of light emitted from the reaction mixture with a standard dose response curve which relates the amount of light emitted to a known concentration of the analyte.

These and other aspects of the invention may be more clearly understood by reference to the following detailed description of the invention and the appended claims.

5. BRIEF DESCRIPTION OF THE DRAWINGS

FIG. 1 illustrates structures of B-AEs with electrophilic N-hydroxysuccinimidyl (NHS) functional groups suitable for preparing conjugates of proteins or other molecules containing nucleophilic functional groups.

FIG. 2 illustrates B-AE structures with nucleophilic, hexaethylene glycol amine (HEG-NH$_2$) functional groups useful for conjugating the acridinium compound to molecules containing electrophilic functional groups.

FIG. 3 shows the structures of estradiol conjugates (abbreviated as B-AE-E2) prepared using the B-AEs of FIG. 2.

6. DESCRIPTION OF THE PREFERRED EMBODIMENTS

The introduction of electron-donating functional groups such as OR* at C2 and/or C7 of the acridinium ring increases the quantum yield of the corresponding chemiluminescent acridinium compound. When the R* group is hydrophilic, such as a sulfopropyl group or methoxy poly (ethylene) glycol, the corresponding acridinium compound not only exhibits increased light output but also shows reduced non-specific binding in immunoassays. These two properties in conjunction lead to an increase in the sensitivity of immunoassays.

The main objectives of the current invention were to identify structural features of acridinium compounds that result in (a) faster light emission when compared to NSP-DMAE and derivatives as well as HQYAE; (b) improved stability especially when compared to HQYAE; (c) high light output that is comparable to HQYAE and (d) low non-specific binding that is comparable to HQYAE.

The hydrophilic acridinium compounds according to the present invention, abbreviated as B-AEs (Branched-Acridinium Esters), not only show increased light output but also show improved stability and faster light emission. By stability we refer to the chemiluminescent activity of the acridinium compounds. An increase in stability is thus manifested as increased retention of chemiluminescent activity as a function of time. Increased stability of acridinium compounds is useful because reagents derived from such compounds are less likely to show a deterioration of assay performance as a function of time and moreover, the shelf life of regents derived from such compounds is likely to be extended thereby leading to less waste. Typically, assay reagents derived from acridinium compounds include conjugates of proteins or small molecules. The second property of the acridinium compounds is faster light emission by which is meant that these compounds emit their total light in a significantly shorter period of time compared to acridinium compounds lacking the unique structural features of the acridinium compounds of the current invention. Faster light emission enables faster measurements in assays and has the potential to increase the throughput of automated analyzers. The throughput of automated analyzers is normally defined as the number of tests the analyzer can perform in a given period of time. The third and fourth properties of the acridinium compounds of the current invention are their increased light output and low non-specific binding, both extremely useful for improving assay sensitivity.

It has unexpectedly been discovered that the placement of branched functional groups derived from glycerol, of the type —OG, where G is a branched functional group, at C2 and/or C7 of the acridinium ring significantly increases the stability of the corresponding acridinium compound and leads to faster light emission. At the same time, the presence of these branched functional groups increases the quantum yield and lowers the non-specific binding of the corresponding acridinium compounds and their conjugates. Non-specific binding in assays using solid phases such as particles or microtiter plates are undesired binding interactions of conjugates to these solid phases. These undesired binding interactions typically increase the background of the assay leading to a net lowering of the signal to background ratio in the assay and thereby decreasing assay sensitivity.

The acridinium compounds of the current invention can be represented by the general formula (I):

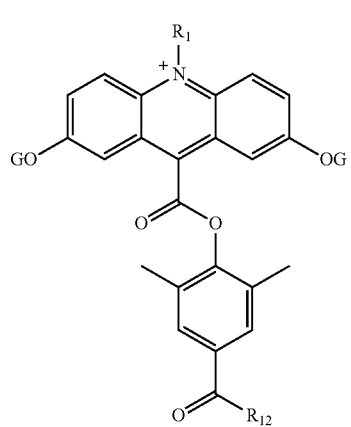

(I)

where $R_1$ is a methyl or sulfopropyl (—$CH_2CH_2CH_2SO_3^-$) group; G is defined as

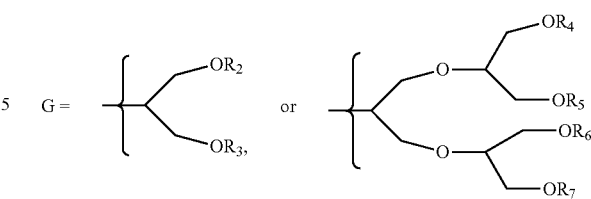

where, $R_2$ and $R_3$ are the same or different and are —$(CH_2CH_2O)_n$Me, where n=1-5; $R_4$, $R_5$, $R_6$ and $R_7$ are the same or different and are either a methyl group or —$(CH_2CH_2O)_n$Me, where n=1-5; and where $R_{12}$ is an electrophilic or nucleophilic group.

More specifically, the acridinium compounds of the present invention can be represented by the following formula:

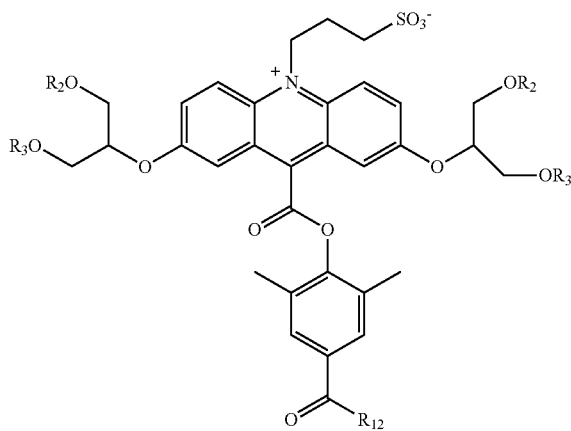

where $R_2$ and $R_3$ are the same or different and are —$(CH_2CH_2O)_n$Me groups, where n=1-3; and where $R_{12}$ is selected from the group consisting of:

(1) —O—N-succinimidyl;
(2) —NH—$(CH_2)_5$—C(=O)—O—N-succinimidyl; and
(3) —NH—$(C_2H_4O)_n$—$C_2H_4$NH—C(=O)—$(CH_2)_3$—C(=O)—O—N-succinimidyl, wherein n=1 to 5; and
(4) —NH—$(C_2H_4O)_n$—$C_2H_4NH_2$ where n=1-5.

The acridinium compounds of the current invention can also be represented by the following formula:

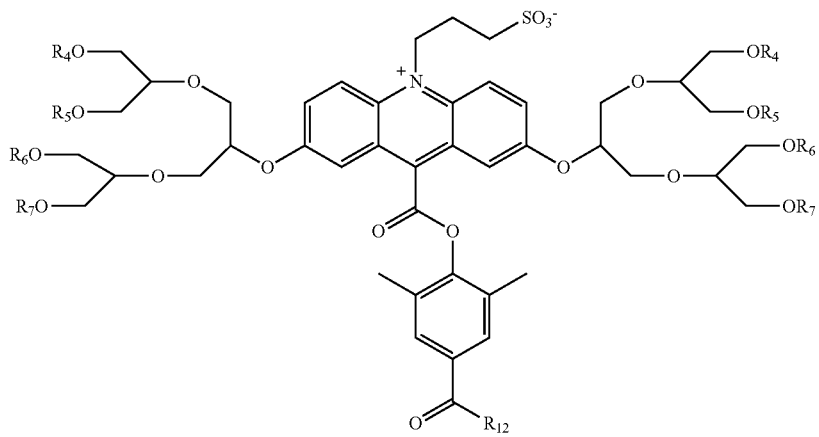

where $R_4$, $R_5$, $R_6$ and $R_7$ are the same or different and are either methyl or —$(CH_2CH_2O)_n$Me, where n=1-3; and where $R_{12}$ is selected from the group consisting of:

(1) —O—N-succinimidyl (NHS);
(2) —NH—$(CH_2)_5$—C(=O)—O—N-succinimidyl; and
(3) —NH—$(C_2H_4O)_n$—$C_2H_4$NH—C(=O)—$(CH_2)_3$—C(=O)—O—N-succinimidyl, wherein n=1 to 5; and
(4) —NH—$(C_2H_4O)_n$—$C_2H_4NH_2$ where n=1-5.

Representative examples of the above general structures were synthesized as discrete structures using traditional organic chemistry techniques. The structures of these compounds along with their abbreviated nomenclature are illustrated in FIGS. 1 and 2. FIG. 1 illustrates structures of B-AEs with electrophilic N-hydroxysuccinimidyl (NHS) functional groups whereas FIG. 2 illustrates B-AE structures with nucleophilic, hexaethylene glycol amine (HEG-$NH_2$) functional groups. The former compounds are suitable for preparing conjugates of proteins or other molecules containing nucleophilic functional groups. The latter compounds are also useful for conjugating the acridinium compound to molecules containing electrophilic functional groups. FIG. 3 shows the structures of estradiol conjugates (abbreviated as B-AE-E2) prepared using the B-AEs of FIG. 2. Estradiol is a steroidal hormone that is commonly measured by immunoassay.

The B-AEs of FIG. 1 as well as NSP-DMAE, NSP-DMAE-HEG-glutarate-NHS (abbreviated as HEG-AE) and the high quantum yield acridinium ester NSP-2,7-(OMHEG) 2-DMAE-AC-NHS (abbreviated as HQYAE) were used to prepare conjugates of a murine, monoclonal anti-TSH antibody (TSH=thyroid stimulating hormone) as described in Example 9. Light emission from each conjugate was triggered by the addition of two reagents. The first reagent comprised 0.5% hydrogen peroxide in 100 mM nitric acid while the second reagent contained a surfactant in 0.25 N sodium hydroxide. Light was measured using a luminometer equipped with a photo-multiplier tube as the detector. The amount of light emitted by each acridinium compound conjugate was reported as Relative Light Units (RLUs) by the luminometer. The total amount of light emitted (100% RLUs) was measured for the various conjugates and light emission at shorter measurement times, are represented as fractions of this number and are also expressed as percentages in Table 1. Other details pertaining to these measurements can be found in the Examples section.

TABLE 1

% RLU as a function of measurement time of acridinium compound-anti-TSH antibody conjugates.

| Entry | Conjugate | 0.5 s | 1.0 s | 2.0 s | 5.0 s |
|---|---|---|---|---|---|
| 1 | HEG-AE | 32 | 65 | 87 | 97 |
| 2 | HQYAE | 31 | 61 | 82 | 95 |
| 3 | B1-AE | 59 | 91 | 96 | 97 |
| 4 | B2-AE | 62 | 91 | 96 | 98 |
| 5 | B3-AE | 57 | 89 | 96 | 97 |
| 6 | B04-AE | 90 | 99 | 99 | 99 |
| 7 | B4-AE | 68 | 95 | 98 | 99 |

From Table 1, while HEG-AE and HQYAE emit only 65% and 61% of their total light in one second, all the B-AE conjugates show much faster light emission with ≥89% of the light emitted in one second. The unique structural features in the B-AEs thus speed up light emission from these compounds when conjugated to a protein.

Similarly, the kinetics of light emission from the B-AE-E2 conjugates illustrated in FIG. 3 was compared with light emission from the E2 conjugates of NSP-DMAE-E2 and HQYAE-E2. Both the latter compounds incorporated the same HEG linkers. The results of these measurements are tabulated in Table 2.

TABLE 2

% RLU as a function of measurement time of E2 conjugates

| Entry | Conjugate | 0.5 s | 1.0 s | 2.0 s | 5.0 s |
|---|---|---|---|---|---|
| 1 | NSP-DMAE | 8 | 23 | 45 | 80 |
| 2 | HQYAE | 35 | 72 | 91 | 98 |
| 3 | B1-AE | 33 | 71 | 93 | 98 |
| 4 | B2-AE | 33 | 70 | 92 | 97 |
| 5 | B4-AE | 39 | 77 | 95 | 99 |

For the estradiol conjugates, all the B-AEs again show faster light emission when compared to NSP-DMAE-HEG-E2 conjugate.

In addition to showing fast light emission, the acridinium esters of the present invention also show good stability. By "stability," is meant a minimal loss of chemiluminescent activity as measured by the loss of RLUs when the compounds or conjugates are stored in an aqueous solution typically, in the pH range of 7-8, which is within the physiological pH. From a mechanistic viewpoint, hydrolysis of the phenolic ester is the main pathway by which chemiluminescent acridinium esters become non-chemiluminescent. Stable conjugates ensure long shelf life for acridinium ester reagents and also ensure that assay performance does not vary greatly over a given period of time. The stability of various acridinium ester conjugates of the current invention are listed in Tables 3 and 4. Aqueous solutions of the conjugates were stored at 37° C. in an aqueous buffer at pH 7.7 and RLUs were recorded periodically using a luminometer. The RLUs that were measured at the initial time point, also referred to as day 0, were assigned a value of 100%. The RLUs that were measured at other time points, are expressed as percentages of this number. Other details pertaining to these measurements can be found in the Examples section.

TABLE 3

Stability of anti-TSH antibody conjugates expressed as % RLU

| Time (days) | HEG-AE | HQYAE | B1-AE | B2-AE | B3-AE | B4-AE |
|---|---|---|---|---|---|---|
| 0 | 100 | 100 | 100 | 100 | 100 | 100 |
| 7 | 94 | 86 | 97 | 91 | 92 | 96 |
| 16 | 89 | 77 | 91 | 85 | 87 | 93 |
| 23 | 82 | 68 | 84 | 78 | 81 | 85 |
| 33 | 82 | 68 | 87 | 79 | 83 | 86 |

TABLE 4

Stability of E2 conjugates expressed as % RLU

| Time (days) | HEG-AE | HQYAE | B1-AE | B2-AE | B4-AE |
|---|---|---|---|---|---|
| 0 | 100 | 100 | 100 | 100 | 100 |
| 1 | 99 | 98 | 97 | 98 | 98 |
| 5 | 95 | 89 | 94 | 94 | 96 |
| 8 | 97 | 87 | 92 | 93 | 96 |
| 12 | 94 | 76 | 89 | 88 | 92 |
| 20 | 92 | 73 | 84 | 85 | 88 |
| 27 | 89 | 66 | 77 | 81 | 84 |
| 33 | 84 | 60 | 75 | 77 | 82 |

As is evident from Tables 3 and 4, the B-AE conjugates retain a greater proportion of their chemiluminescent activity and are more stable compared to the HQYAE conjugate. For example, the anti-TSH antibody conjugate of HQYAE retains 68% of its chemiluminescent activity after 33 days at 37° C., the B-AE conjugates retain ≥79% of their chemiluminescent activity in the same period of time. A similar trend is noted for the estradiol (E2) conjugates where the B-AE conjugates retain ≥75% of their chemiluminescent activity after 33 days at 37° C., whereas the HQYAE conjugate's chemiluminescent activity has dropped to 60% in the same time period.

In addition to showing fast light emission, the B-AEs of the present invention also show increased light output that is comparable to or better than HQYAE. Table 5 summarizes the relative quantum yields of the various B-AEs when conjugated to the anti-TSH monoclonal antibody. In this table, the quantum yield of HEG-AE was assigned a value of unity (1) and the quantum yields of all the other conjugates are relative to this conjugate of this compound.

TABLE 5

Relative quantum yields of AE conjugates of anti-TSH antibody

| Entry | Conjugate | Relative quantum yield |
|---|---|---|
| 1 | HEG-AE | 1.0 |
| 2 | HQYAE | 2.2 |
| 3 | B1-AE | 4.7 |
| 4 | B2-AE | 2.7 |
| 5 | B3-AE | 1.9 |
| 6 | B04-AE | 1.5 |
| 7 | B4-AE | 2.0 |

As can be noted from Table 5, all the B-AE conjugates show greater light output (higher quantum yield) than the HEG-AE conjugate and are either comparable or greater than the light output of the HQYAE conjugate.

Finally, the B-AEs of the current invention also show low non-specific binding to solid phases (Table 6). Non-specific binding, as described earlier, in assays using solid phases such as particles or microtiter plates are undesired binding interactions of conjugates to these solid phases. These undesired binding interactions typically increase the background of the assay leading to a net lowering of the signal to background ratio in the assay and thereby decreasing assay sensitivity. For the various acridinium conjugates of the anti-TSH antibody listed in Table 6, non-specific binding was measured on two different kinds of particles; paramagnetic particles (PMP) and magnetic latex particles (MLP). These two particles differ in their intrinsic composition. PMPs are made mainly of iron oxide particles with a silane coating containing amines. The amines are used to cross-link proteins to the particle surface using reagents such as glutaraldehyde. MLPs on the other hand are made of polystyrene. The MLPs used in Table 6 contained a thin layer of magnetite to enable magnetic separation and a polyacrylic acid coating for conjugating proteins. The two types of particles were mixed with solutions of the conjugates for a specific period of time and then the particles were magnetically separated, washed once and then the chemiluminescence associated with the particles was measured. (Experimental details can be found in Example 11.) The ratio of this chemiluminescence value in comparison to the total chemiluminescence input is referred to fraction non-specific binding (fNSB). Conjugates with low non-specific binding will have low fNSB values. In examining Table 6, it is evident that all the B-AE conjugates have lower non-specific binding than HEG-AE on both types of particles. The fNSB values of the B-AE conjugates were also found to be comparable to the previously described hydrophilic HQYAE.

TABLE 6

Fractional Nonspecific Binding (fNSB) of anti-TSH antibody-acridinium conjugates to particles.

| | Particle | |
|---|---|---|
| | PMP | MLP |
| Acridinium Ester Conjugate | Fractional Nonspecific Binding (fNSB) | |
| HEG-AE | 4.1E−05 | 1.2E−05 |
| HQYAE | 6.0E−06 | 7.5E−07 |
| B1-AE | 4.5E−06 | 1.8E−06 |
| B2-AE | 5.9E−06 | 2.8E−06 |
| B3-AE | 3.9E−06 | 1.2E−06 |
| B4-AE | 5.8E−06 | 1.9E−06 |
| B04-AE | 5.9E−06 | 7.1E−06 |

The hydrolytically stable, fast light emitting, hydrophilic, high quantum yield acridinium compounds of the invention are useful as labels in assays for the determination or quantitation of analytes. Analytes that are typically measured in such assays are often substances of some clinical relevance and can span a wide range of molecules from large macromolecules such as proteins, nucleic acids, viruses bacteria, etc. to small molecules such as ethanol, vitamins, steroids, hormones, therapeutic drugs, etc. A 'sandwich' immunoassay typically involves the detection of a large molecule, also referred to as macromolecular analyte, using two binding molecules such as antibodies. One antibody is immobilized or attached to a solid phase such as a particle, bead, membrane, microtiter plate or any other solid surface. Methods for the attachment of binding molecules such as antibodies to solid phases are well known in the art. For example, an antibody can be covalently attached to a particle containing amines on its surface by using a cross-linking molecule such as glutaraldehyde. The attachment may also be non-covalent and may involve simple adsorption of the binding molecule to the surface of the solid phase, such as polystyrene beads and microtiter plate. The second antibody is often covalently attached with a chemiluminescent or fluorescent molecule often referred to as a label. Labeling of binding molecules such as antibodies and other binding proteins are also well known in the art and are commonly called conjugation reactions and the labeled antibody is often called a conjugate. Typically, an amine-reactive moiety on the label reacts with an amine on the antibody to form an amide linkage. Other linkages such as thioether, ester, carbamate, and the like, between the antibody and the label are also well known. In the assay, the two antibodies bind to different regions of the macromolecular analyte. The macromolecular analyte can be, for example, proteins, nucleic acids, oligosaccharides, antibodies, antibody fragments, cells, viruses, receptors, or synthetic polymers. The binding molecules can be antibodies, antibody fragments, nucleic acids, peptides, binding proteins or synthetic binding polymers. For example the folate binding protein ("FBP") binds the analyte folate. Synthetic binding molecules that can bind a variety of analytes have also been disclosed by Mossbach et al. *Biotechnology vol.* 14, pp. 163-170 (1995).

When the solid phase with the immobilized antibody and the labeled antibody is mixed with a sample containing the analyte, a binding complex is formed between the analyte and the two antibodies. This type of assay is often called a heterogenous assay because of the involvement of a solid phase. The chemiluminescent or fluorescent signal associated with the binding complex can then be measured and the presence or absence of the analyte can be inferred. Usually, the binding complex is separated from the rest of the binding reaction components such as excess, labeled antibody prior to signal generation. For example if the binding complex is associated with a magnetic bead, a magnet can be used to separate the binding complex associated with the bead from bulk solution. By using a series of 'standards', that is, known concentrations of the analyte, a 'dose-response' curve can be generated using the two antibodies. Thus, the dose-response curve correlates a certain amount of measured signal with a specific concentration of analyte. In a sandwich assay, as the concentration of the analyte increases, the amount of signal also increases. The concentration of the analyte in an unknown sample can then be calculated by comparing the signal generated by an unknown sample containing the macromolecular analyte, with the dose-response curve.

In a similar vein, the two binding components can also be nucleic acids that bind or hybridize to different regions of a nucleic acid analyte. The concentration of the nucleic acid analyte can then be deduced in a similar manner.

Another class of immunoassays for small molecule analytes such as steroids, vitamins, hormones, therapeutic drugs or small peptides employs an assay format that is commonly referred to as a competitive assay. Typically, in a competitive assay, a conjugate is made of the analyte of interest and a chemiluminescent or fluorescent label by covalently linking the two molecules. The small molecule analyte can be used as such or its structure can be altered prior to conjugation to the label. The analyte with the altered structure is called an analog. It is often necessary to use a structural analog of the analyte to permit the chemistry for linking the label with the analyte. Sometimes a structural analog of an analyte is used to attenuate or enhance its binding to a binding molecule such an antibody. Such techniques are well known in the art. The antibody or a binding protein to the analyte of interest is often immobilized on a solid phase either directly or through a secondary binding interaction such as the biotin-avidin system.

The concentration of the analyte in a sample can be deduced in a competitive assay by allowing the analyte-containing sample and the analyte-label conjugate to compete for a limited amount of solid phase-immobilized binding molecule. As the concentration of analyte in a sample increases, the amount of analyte-label conjugate captured by the binding molecule on the solid phase decreases. By employing a series of 'standards', that is, known concentrations of the analyte, a dose-response curve can be constructed where the signal from the analyte-label conjugate captured by the binding molecule on the solid phase is inversely correlated with the concentration of analyte. Once a dose-response curve has been devised in this manner, the concentration of the same analyte in an unknown sample can be deduced by comparing the signal obtained from the unknown sample with the signal in the dose-response curve.

Another format of the competitive assay for small molecules analytes involves the use of a solid phase that is immobilized with the analyte of interest or an analyte analog and an antibody or a binding protein specific for the analyte that is conjugated with a chemiluminescent or fluorescent label. In this format, the antibody-label conjugate is captured onto the solid phase through the binding interaction with the analyte or the analyte analog on the solid phase. The analyte of interest present in a sample then "competitively" binds to the antibody-label conjugate and thus inhibits or replaces the interaction of the antibody-label conjugate with the solid phase. In this fashion, the amount of signal generated from the antibody-label conjugate captured on the solid phase is correlated to the amount of the analyte in sample.

In accordance with the foregoing, an assay for the detection or quantification of an analyte comprises, according to one embodiment of the invention, the following steps:

(a) providing a conjugate comprising: (i) a binding molecule specific for an analyte; and (ii) any of the inventive hydrophilic, high quantum yield and fast light emitting acridinium esters according to the invention;

(b) providing a solid support having immobilized thereon a second binding molecule specific for said analyte;

(c) mixing the conjugate, the solid phase and a sample suspected of containing the analyte to form a binding complex;

(d) separating the binding complex captured on the solid support;

(e) triggering chemiluminescence of the binding complex from step (d) by adding chemiluminescence triggering reagents;

(f) measuring the amount of light emission with a luminometer; and (g) detecting the presence or calculating the concentration of the analyte by comparing the amount of light emitted from the reaction mixture with a standard dose response curve which relates the amount of light emitted to a known concentration of the analyte.

In another embodiment, an assay for the detection or quantification of an analyte is provided comprising the steps of:

(a) providing a conjugate of an analyte with any of the any of the inventive hydrophilic, high quantum yield and fast light emitting acridinium esters (b) providing a solid support immobilized with a binding molecule specific for the analyte;

(c) mixing the conjugate, solid support and a sample suspected of containing the analyte to form a binding complex;

(d) separating the binding complex captured on the solid support;

(e) triggering the chemiluminescence of the binding complex from step (d) by adding chemiluminescence triggering reagents;

(f) measuring the amount of light with an luminometer; and (g) detecting the presence or calculating the concentration of the analyte by comparing the amount of light emitted from the reaction mixture with a standard dose response curve which relates the amount of light emitted to a known concentration of the analyte.

Macromolecular analytes can be proteins, nucleic acids, oligosaccharides, antibodies, antibody fragments, cells, viruses, synthetic polymers, and the like. Small molecule analytes can be steroids, vitamins, hormones, therapeutic drugs, small peptides, and the like. The binding molecules in the assays can be an antibody, an antibody fragment, a binding protein, a nucleic acid, a peptide, a receptor or a synthetic binding molecule.

Example 1

Synthesis of B1-AE-NHS ester, 1i a) 1,3-Bis(methoxyethoxy)-2-propyl toluenesulfonate, 1b The compound 1a, 1,3-bis(methoxyethoxy)-2-propanol was synthesized as described by Cormier and Gregg in *Chem. Mater.* 1998, 10, 1309-1319. A solution of 1a (2 g, 9.6 mmol) in anhydrous pyridine (10 mL) was treated with 4-dimethylaminopyridine (0.234 g, 1.92 mmol) followed by p-toluenesulfonyl chloride (3.67 g, 19.25 mmol). The reaction was stirred at room temperature under a nitrogen atmosphere for 3 days. The solvent was then removed under reduced pressure and the residue was partitioned between ethyl acetate (75 mL) and 10% HCl (100 mL). The ethyl acetate layer was washed with brine, dried over anhydrous magnesium sulfate and concentrated under reduced pressure. The crude product (4.05 g) was purified by flash chromatography on silica gel using 1:1, ethyl acetate/hexanes as eluent. The product was recovered as a light yellow oil. Yield=2.42 g (70%).

b) Compound 1d

A mixture of 2,7-dihydroxy acridine methyl ester, 1c (0.2 g, 0.48 mmol), (U.S. Pat. No. 7,309,615), compound 1b (0.868 g, 2.39 mmol) and cesium carbonate (0.39 g, 1.2 mmol) in anhydrous DMF (10 mL) was heated at 100° C. under a nitrogen atmosphere for 4-5 hours. A small portion of the reaction mixture was then analyzed by HPLC using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=25 minutes and was the major component. The reaction was then cooled to room temperature and concentrated under reduced pressure. The residue was partitioned between ethyl acetate (50 mL) and water (50 mL). The ethyl acetate layer was separated, dried over anhydrous magnesium sulfate and concentrated under reduced pressure. The crude product (0.48 g) was purified by flash chromatography on silica gel using ethyl acetate as eluent. Yield=0.134 g (34%); MALDI-TOF MS 797.8 observed.

c) Compound 1f

A mixture of compound 1d (60 mg, 75.3 umoles), distilled 1,3-propane sultone (1 g, 8.2 mmol) and sodium bicarbonate (65 mg, 0.77 mmol) was heated at 150° C. under a nitrogen atmosphere for 1 hour. A portion of the reaction mixture was withdrawn, diluted with methanol and analyzed by HPLC as described in section (b). The acridinium ester 1e was observed eluting at Rt=19 minutes. The reaction was cooled to room temperature and 20 mL of 1:1, ethyl acetate/hexanes was added. The mixture was sonicated briefly to disperse the gummy solid and the solvent was then decanted. The crude product was dried under reduced pressure. This crude product was suspended in 1 N HCl (10 mL) and was refluxed under a nitrogen atmosphere for 2 hours. HPLC analysis of the crude reaction mixture showed complete hydrolysis of the reaction mixture with product eluting at Rt=16 minutes. The product was purified by preparative HPLC using an YMC, $C_{18}$ 30×300 mm column and the same gradient at described in section (b) at a solvent flow rate of 20 mL/minute and UV detection at 260 nm. The HPLC fractions containing product were combined and concentrated under reduced pressure. Yield=55 mg (81%); MALDI-TOF MS 904.7 observed.

d) Compound 1g

A solution of compound 1f (53 mg, 58.2 umoles) in anhydrous DMF (2 mL) was treated with diisopropylethylamine (15.2 uL, 87.3 umoles) and TSTU (20 mg, 64 umoles). The reaction was stirred at room temperature. After 30 minutes, HPLC analysis of the reaction mixture as described in section (b) indicated complete conversion to the NHS ester eluting at Rt=18 minutes. This reaction was added dropwise to a stirred solution of 2,2'-(ethylenedioxy) bis(ethylamine) (86 ul, 0.582 mmol) in anhydrous DMF (1.0 mL). After 30 minutes, HPLC analysis of the reaction mixture, as described in section (b) showed complete conversion to the product 1g eluting at Rt=13.6 minutes. The product was purified by preparative HPLC as described in section (c). Yield=50 mg (83%); MALDI-TOF MS 1035.6 observed.

e) B1-AE-NHS, Compound 1i

A solution of compound 1g (47.5 mg, 46 umoles) in anhydrous methanol (3 mL) was treated with diisopropylethylamine (40 uL, 0.23 mmol) and glutaric anhydride (26 mg, 0.23 mmol). The reaction was stirred at room temperature. After 30 minutes, HPLC analysis, as described in section (b), showed complete conversion to the glutarate derivative 1h eluting at Rt=14.8 minutes. The reaction mixture was diluted with anhydrous toluene (3 mL) and concentrated under reduced pressure. The crude product was dissolved in anhydrous DMF (3 mL) and treated with diisopropylethylamine (80 uL, 0.46 mmol) and TSTU (138 mg, 0.46 mmol). After stirring for 30 minutes, HPLC analysis, as described in section (b), showed >80% conversion to the product 1i eluting at Rt=16 minutes. The product was purified by preparative HPLC as described in section (c). The HPLC fractions containing product were frozen at −80° C. and lyophilized to dryness. The lyophilized product was dissolved in anhydrous MeCN and transferred to a tared round bottom flask and concentrated under reduced pressure. Yield=32 mg (56%); MALDI-TOF MS 1247.1 observed.

The following reactions describe the synthesis of B1-AE-NHS, compound 1i.

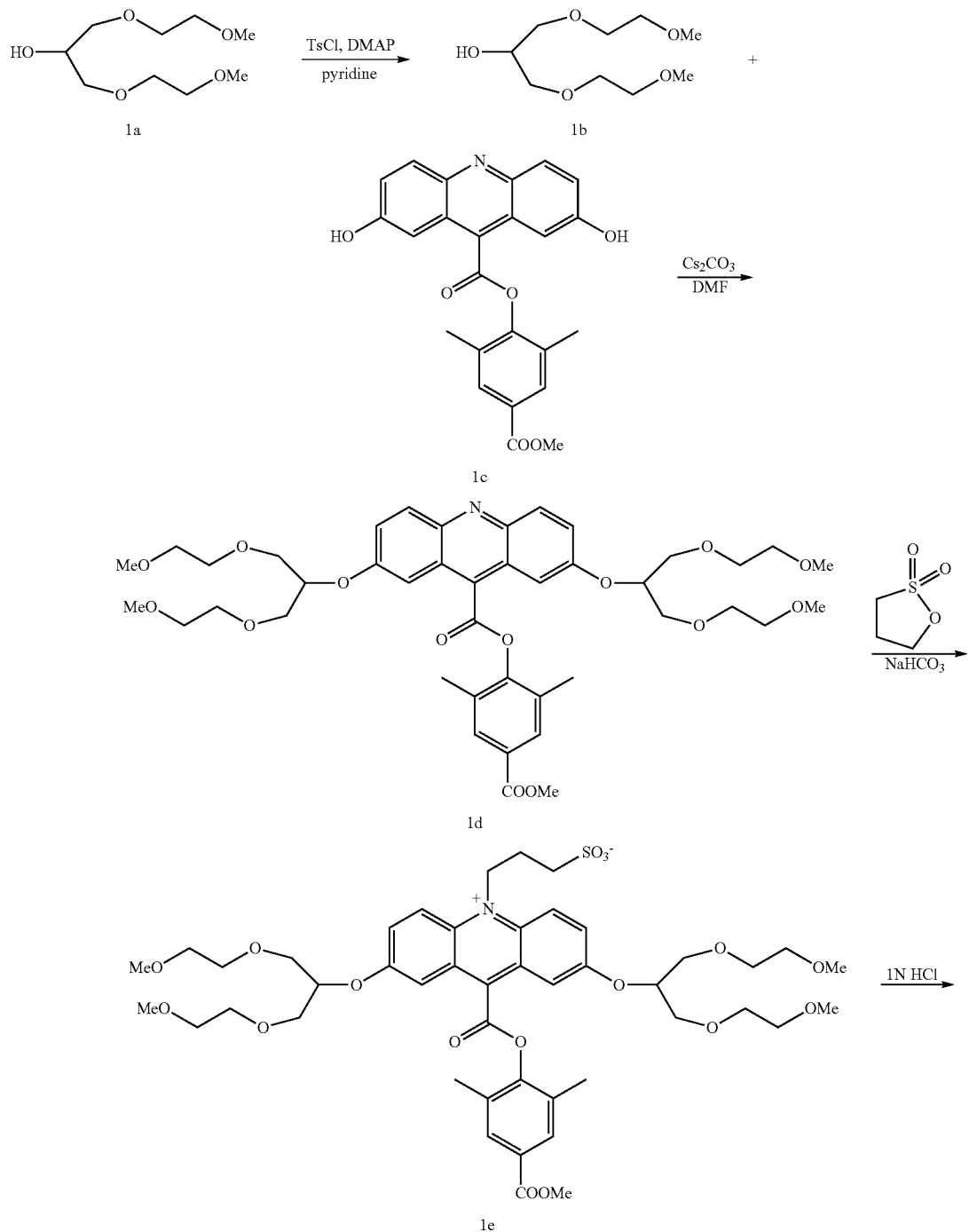

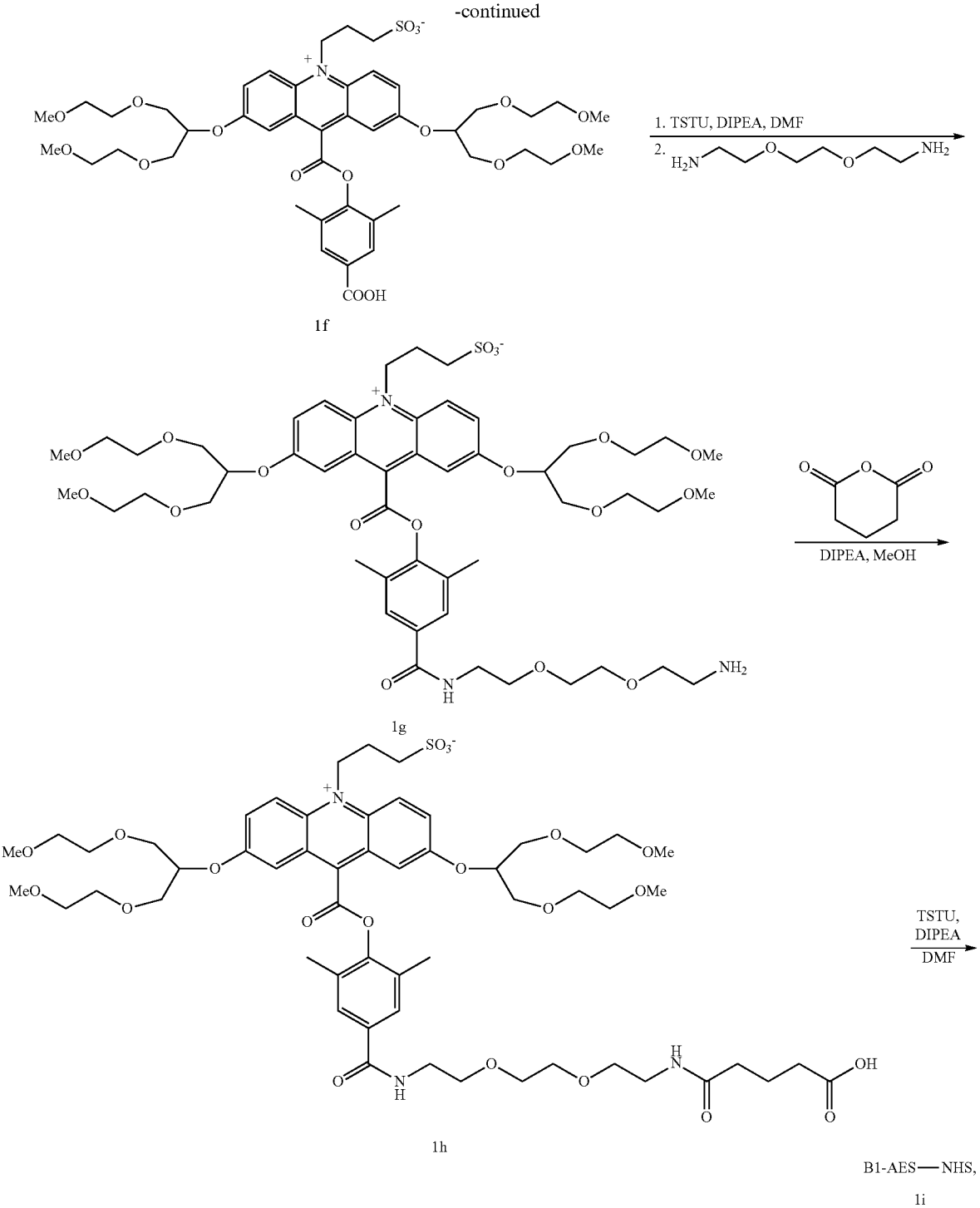

Example 2

Synthesis of B2-AE-NHS ester, 2h a). 1,3-Bis(3,6-dioxaheptanyl)glycerol-2-toluenesulfonate, 2b The compound 1,3-Bis(3,6-dioxaheptanyl)glycerol, 2a, was synthesized as described by Vacus and Simon in *Adv. Mater.* 1995, 7, 797-800. Crude 2a (16 g, 0.054 mol) was dissolved in anhydrous pyridine (50 mL) and treated with 4-dimethylaminopyridine (1.32 g, 0.011 mol) followed by p-toluenesulfonyl chloride (12.4 g, 0.065 mol). The reaction was stirred under a nitrogen atmosphere for 16 hours. The solvent was then removed under reduced pressure and the residue was partitioned between ethyl acetate (100 mL) and 2N HCl (100 mL). The ethyl acetate layer was washed with saturated sodium bicarbonate solution followed by brine. It was then dried over magnesium sulfate and concentrated under reduced pressure. The crude product (14 g) was purified by flash chromatography on silica gel using 1:4, hexanes/ethyl acetate as eluent. Yield=6.3 g, light yellow oil. MALDI-TOF MS 473.4 observed, (M+Na$^+$).

b) Compound 2c

A mixture of 1c (0.2 g, 0.48 mmol), 2b (1.08 g, 2.4 mmol) and cesium carbonate (0.39 g, 0.12 mmol) in anhydrous DMF (10 mL) was heated in an oil bath at 100° C. under a nitrogen atmosphere. After 5 hours, the reaction was cooled to room temperature and concentrated under reduced pressure. The residue was partitioned between ethyl acetate (75 mL) and water (75 mL). The ethyl acetate layer was washed with brine and dried over anhydrous magnesium sulfate. The solvent was then removed under reduced pressure to afford 0.974 g of crude product which was purified by flash chromatography on silca gel using 3% methanol in ethyl acetate as eluent. Yield=99.4 mg (21%); MALDI-TOF MS 974.4 observed.

c) Compound 2e

A mixture of compound 2c (58 mg, 60 umoles), distilled 1,3-propane sultone (0.75 g, 6.15 mmol) and sodium bicarbonate (50 mg, 0.59 mmol) was heated at 150° C. under a nitrogen atmosphere. After 1 hour, a small portion was withdrawn, diluted with methanol and analyzed by HPLC using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=18.5 minutes (>80% conversion, starting material Rt=23.5 minutes). The reaction was cooled to room temperature and 20 mL of 1:1, ethyl acetate/hexanes was added. After brief sonication to disperse the gummy product, the solvent was decanted and the product 2d was dried under vacuum.

The crude acridinium ester 2d was suspended in 1 N HCl (10 mL) and refluxed under a nitrogen atmosphere for 2 hours. HPLC analysis, as described above, indicated complete conversion to product 2e eluting at 16 minutes. The product was purified by preparative HPLC using an YMC, $C_{18}$ 30×300 mm column and the same gradient described above at a solvent flow rate of 20 mL/minute and UV detection at 260 nm. The HPLC fractions containing product were combined and concentrated under reduced pressure. Yield=42 mg (65%); MALDI-TOF MS 1083.3 observed.

d) Compound 2f

A solution of compound 2e (42 mg, 39 umoles) in anhydrous DMF (2 mL) was treated with diisopropylethylamine (10 uL, 59 umoles) and TSTU (14 mg, 46.5 umoles). The reaction was stirred at room temperature. After 15 minutes, HPLC analysis, as described in section (c) showed complete conversion to the NHS ester eluting at Rt=17.7 minutes. This reaction was added dropwise to a stirred solution of 2,2'-(ethylenedioxy)bis(ethylamine) (58 ul, 0.39 mmol) in anhydrous DMF (1.0 mL). After 30 minutes, HPLC analysis of the reaction mixture, as described in section (b) showed complete conversion to the product 2f eluting at Rt=13.6 minutes. The product was purified by preparative HPLC as described in section (c). Yield=37 mg (79%); MALDI-TOF MS 1217.9 observed.

e) B2-AE-NHS, Compound 2h

A solution of compound 2f (37 mg, 30 umoles) in anhydrous methanol (3 mL) was treated with diisopropylethylamine (26 uL, 0.15 mmol) and glutaric anhydride (17 mg, 0.15 mmol). The reaction was stirred at room temperature. After 30 minutes, HPLC analysis, as described in section (c), showed complete conversion to the glutarate derivative 2g eluting at Rt=15 minutes. The reaction mixture was diluted with anhydrous toluene (3 mL) and concentrated under reduced pressure. The crude product was dissolved in anhydrous DMF (2 mL) and treated with diisopropylethylamine (52 uL, 0.3 mmol) and TSTU (89 mg, 0.3 mmol). After stirring for 30 minutes, HPLC analysis, as described in section (c), showed >80% conversion to the product 2h eluting at Rt=16 minutes. The product was purified by preparative HPLC as described in section (c). The HPLC fractions containing product were frozen at −80° C. and lyophilized to dryness. The lyophilized product was dissolved in anhydrous MeCN and transferred to a tared round bottom flask and concentrated under reduced pressure. Yield=39 mg (91%); MALDI-TOF MS 1425.4 observed.

The following reactions describe the synthesis of B2-AE-NHS, 2h.

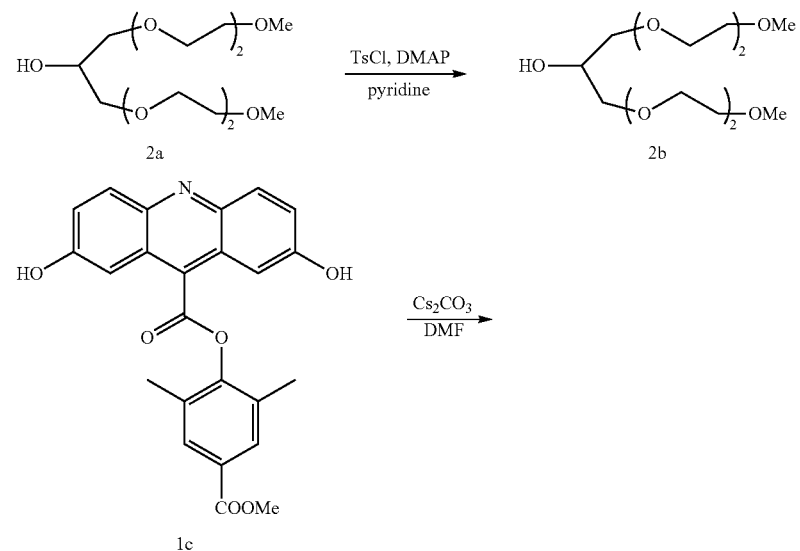

-continued
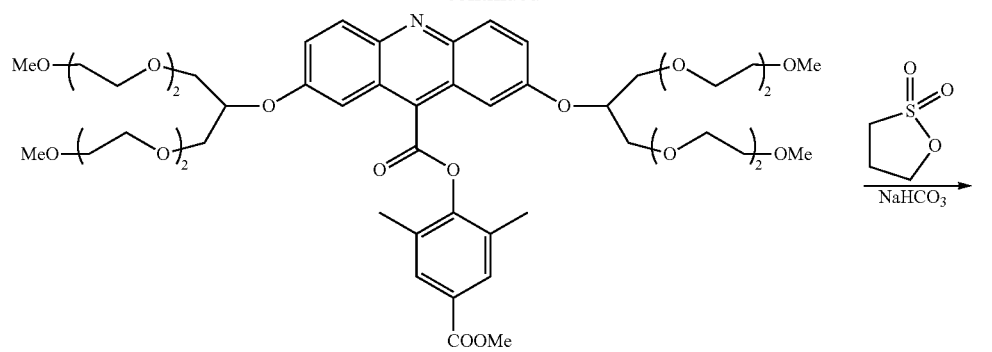 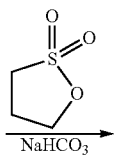
2c
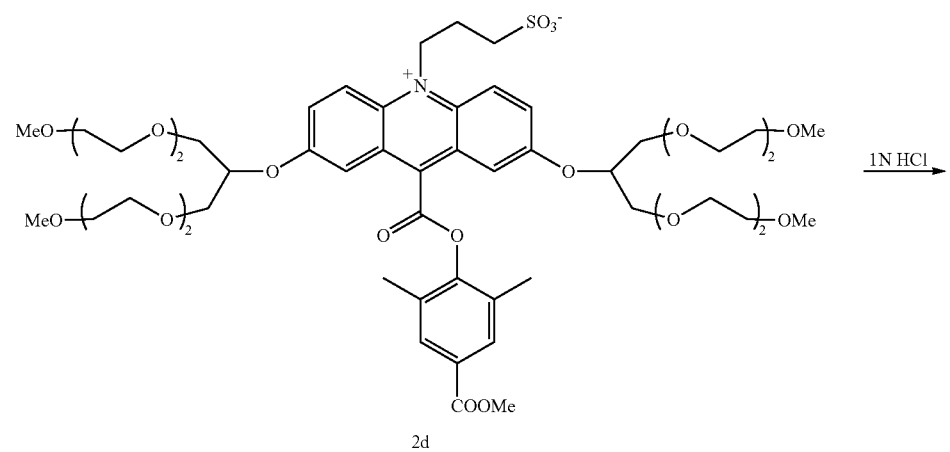
2d
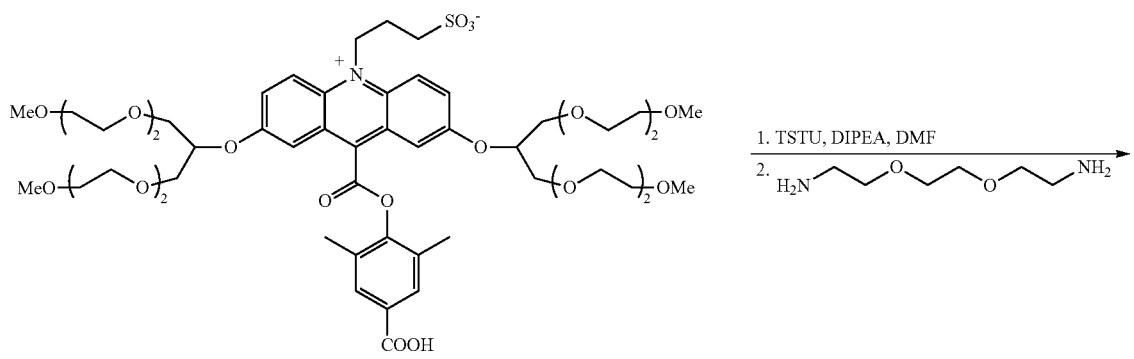
2e
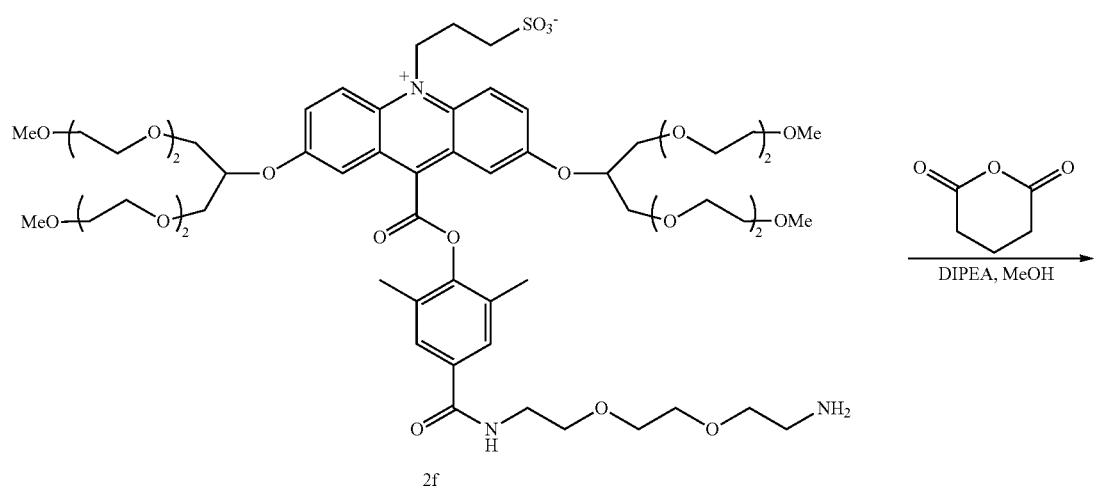 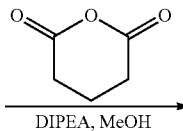
2f

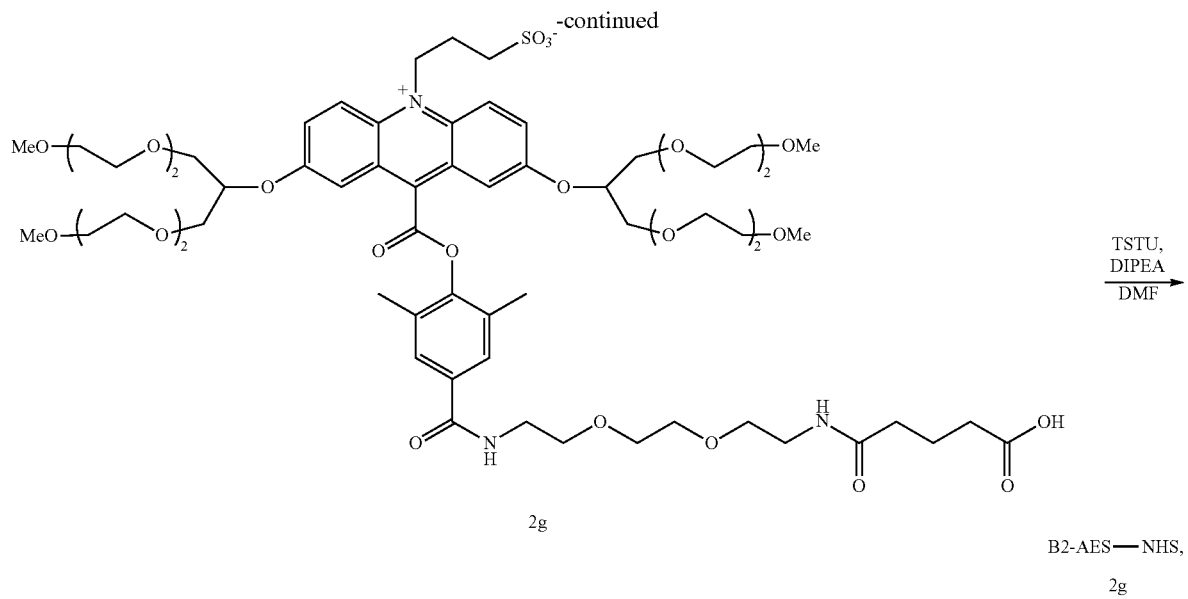

Example 3

B3-AE-NHS Ester 3h a) 1,3-Bis(3,6,9-dioxadecanyl)glycerol-2-toluenesulfonate, 3b

The compound 1,3-Bis(3,6,9-dioxadecanyl)glycerol, 3a, was synthesized as described by Lauter et al. in *Macromol. Chem. Phys.* 1998, 199, 2129-2140. The alcohol (7 g, 0.0182 mol) was dissolved in anhydrous pyridine (30 mL) and treated with 4-dimethylaminopyridine (0.444 g, 3.6 mmol) and p-toluenesulfonyl chloride (3.85 g, 0.02 mol). The reaction was stirred under a nitrogen atmosphere for 3 days. The solvent was then removed under reduced pressure and the residue was partitioned between ethyl acetate (100 mL) and 10% HCl (100 mL). The ethyl acetate layer was washed with saturated sodium bicarbonate solution and brine. It was then dried over anhydrous magnesium sulfate and concentrated under reduced pressure. The crude product was purified by flash chromatography on silica gel using 5:4.5:0.5, hexanes:ethyl acetate:methanol. Yield=4.47 g (45%); light yellow oil.

b) Compound 3c

A mixture of 1c (0.2 g, 0.48 mmol), 3b (1.3 g, 2.4 mmol) and cesium carbonate (0.35 g, 0.11 mmol) in anhydrous DMF (10 mL) was heated in an oil bath at 100° C. under a nitrogen atmosphere. After 6 hours, the reaction was cooled to room temperature and concentrated under reduced pressure. The residue was partitioned between ethyl acetate (75 mL) and water (75 mL). The ethyl acetate layer was washed with brine and dried over anhydrous magnesium sulfate. The solvent was then removed under reduced pressure to afford 1.3 g of crude product which was purified by flash chromatography on silica gel using 5% methanol in ethyl acetate as eluent. Yield=134 mg (22%); MALDI-TOF MS 1148.9 observed.

c) Compound 3e

A mixture of compound 3c (45 mg, 39 umoles), distilled 1,3-propane sultone (0.5 g, 4.1 mmol) and sodium bicarbonate (33 mg, 0.39 mmol) was heated at 150° C. under a nitrogen atmosphere. After 2 hours, a small portion was withdrawn, diluted with methanol and analyzed by HPLC using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=18.3 minutes (>80% conversion, starting material Rt=22.5 minutes). The reaction was cooled to room temperature and 20 mL of 1:1, ethyl acetate/hexanes was added. After brief sonication to disperse the gummy product, the solvent was decanted and the product 3d was dried under vacuum.

The crude acridinium ester 3d was suspended in 1 N HCl (10 mL) and refluxed under a nitrogen atmosphere for 2 hours. HPLC analysis, as described above, indicated complete conversion to product 3e eluting at 16.3 minutes. The product was purified by preparative HPLC using an YMC, $C_{18}$ 30×300 mm column and the same gradient at described above at a solvent flow rate of 20 mL/minute and UV detection at 260 nm. The HPLC fractions containing product were combined and concentrated under reduced pressure. Yield=28 mg (57%); MALDI-TOF MS 1255.9 observed.

d) Compound 3f

A solution of compound 3e (28 mg, 22.3 umoles) in anhydrous DMF (2 mL) was treated with diisopropylethylamine (6.4 uL, 33.5 umoles) and TSTU (8 mg, 26.6 umoles). The reaction was stirred at room temperature. After 30 minutes, HPLC analysis, as described in section (c) showed complete conversion to the NHS ester eluting at Rt=17.7 minutes. This reaction was added dropwise to a stirred solution of 2,2'-(ethylenedioxy)bis(ethylamine) (32 ul, 0.22 mmol) in anhydrous DMF (1.0 mL). After one hour, HPLC analysis of the reaction mixture, as described in section (c) showed complete conversion to the product 3f eluting at Rt=14 minutes. The product was purified by preparative HPLC as described in section (c). Yield=28 mg (90%); MALDI-TOF MS 1388.6 observed.

e) B3-AE-NHS, Compound 3h

A solution of compound 3f (28 mg, 20 umoles) in anhydrous methanol (2 mL) was treated with diisopropylethylamine (17.6 uL, 0.1 mmol) and glutaric anhydride (11.5 mg, 0.1 mmol). The reaction was stirred at room temperature. After 30 minutes, HPLC analysis, as described in section (c), showed complete conversion to the glutarate derivative 3g eluting at Rt=15.2 minutes. The reaction mixture was diluted with anhydrous toluene (3 mL) and concentrated under reduced pressure. The crude product was dissolved in anhydrous DMF (2 mL) and treated with diisopropylethylamine (35 uL, 0.2 mmol) and TSTU (60 mg, 0.2 mmol). After stirring for 30 minutes, HPLC analysis, as described in section (c), showed >70% conversion to the product 3h eluting at Rt=16.2 minutes. The product was purified by preparative HPLC as described in section (c). The HPLC fractions containing product were frozen at −80° C. and lyophilized to dryness. The lyophilized product was dissolved in anhydrous MeCN and transferred to a tared round bottom flask and concentrated under reduced pressure. Yield=17.6 mg (55%); MALDI-TOF MS 1598 observed.

The following reactions describe the synthesis of B3-AE-NHS, 3h.

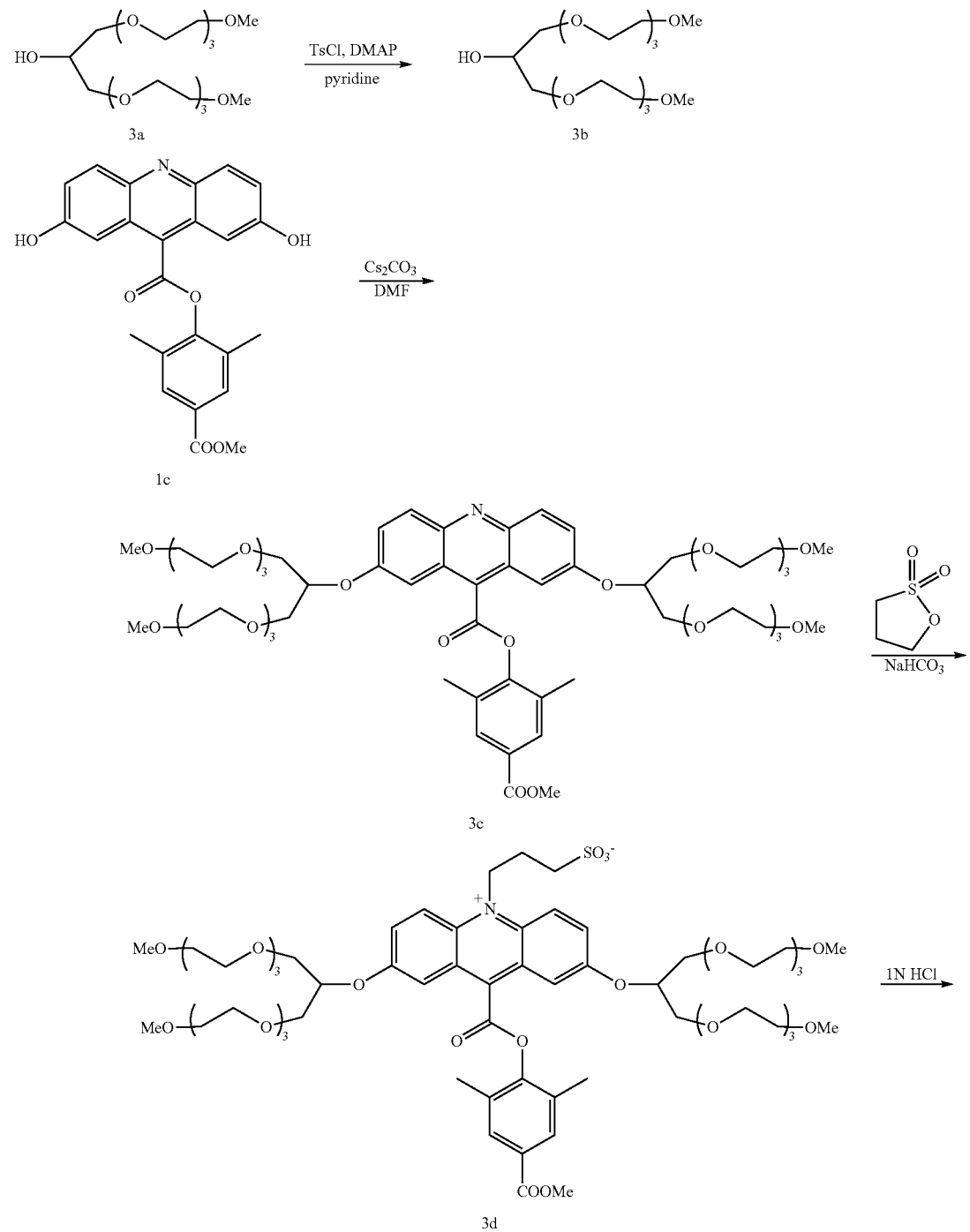

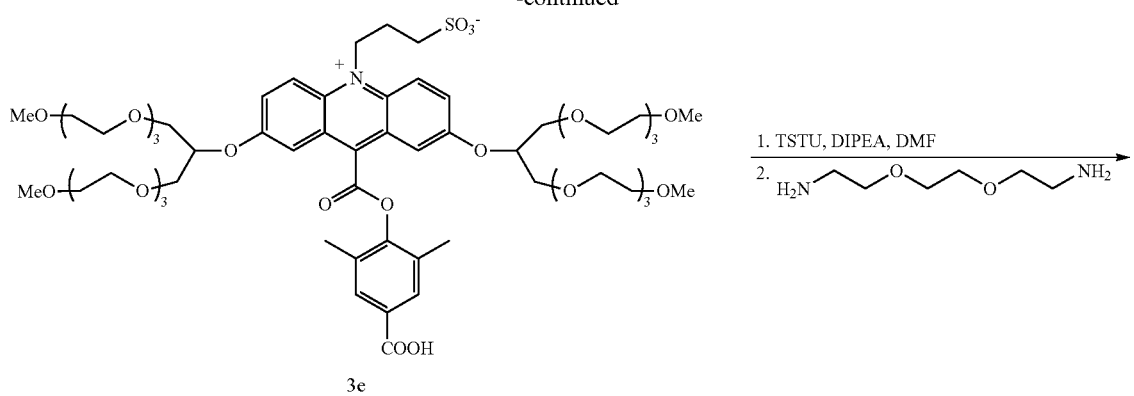
3e
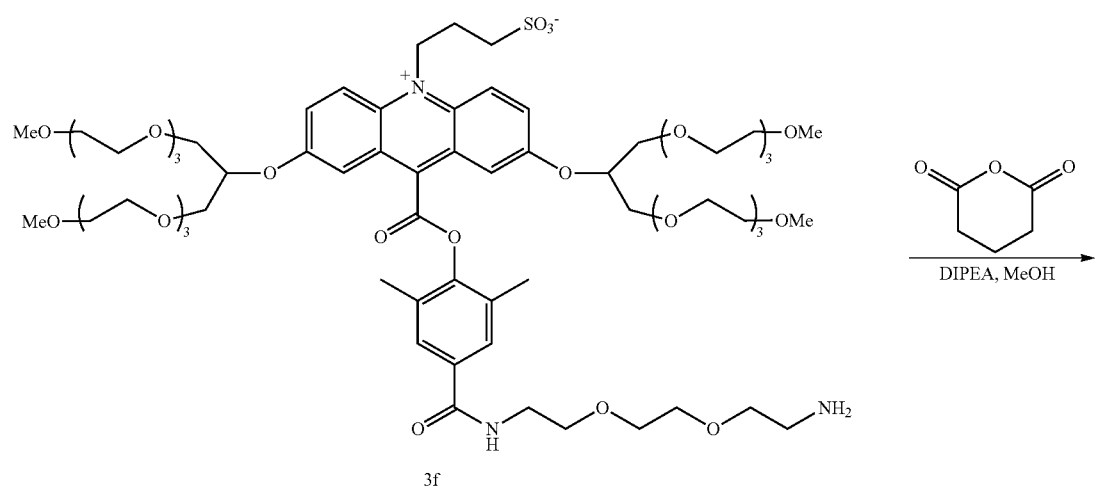
3f
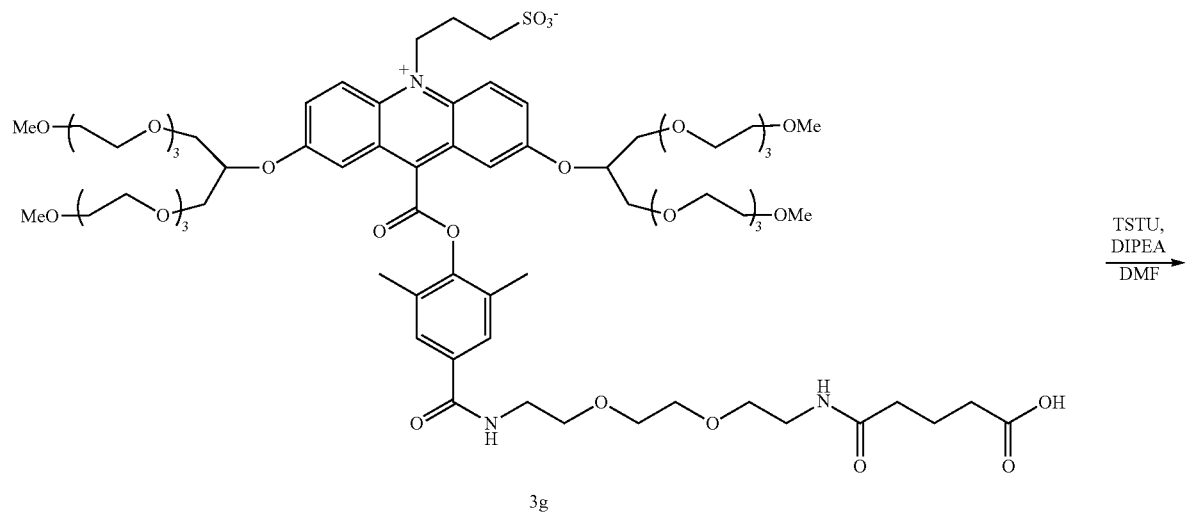
3g
B3-AE—NHS,
3h

Example 4

B4-AE-NHS Ester, 4h a) Compound 4a 1,3-Bis(methoxyethoxy)-2-propanol, 1a, (12 g, 0.058 mol) and potassium hydroxide (2.43 g, 0.043 mol) were stirred vigorously and epichlorohydrin (1.334 g, 0.0144 mol) was added dropwise. The reaction was heated at 80° C. for 24 hours. It was then cooled to room temperature and water (50 mL) was added. The solution was extracted with dichloromethane (3×50 mL). The combined dichloromethane extracts were dried over anhydrous magnesium sulfate and concentrated under reduced pressure. The crude product (10.85 g) was sued as such for the next reaction.

b) Compound 4b

A solution of 4a (10.5 g crude, 0.023 mol) in anhydrous pyridine (25 mL) was treated with 4-dimethylaminopyridine (0.56g, 4.6 mmol) and p-toluenesulfonyl chloride (0.046 mol, 8.8 g). The reaction was stirred at room temperature under a nitrogen atmosphere for 16 hours. The solvent was then removed under reduced pressure and the residue was partitioned between ethyl acetate (100 mL) and 2 N HCl (100 mL). The ethyl acetate layer was washed with saturated sodium bicarbonate and brine. It was then dried over anhydrous magnesium sulfate and concentrated under reduced pressure. The crude product (16.4 g) was purified by flash chromatography on silica gel using 1:1 ethyl acetate:hexanes to elute 1,3-bis(methoxyethoxy)-2-propyl toluenesulfonate followed by ethyl acetate to elute product. Yield=2.82 g (32%); MALDI-TOF MS 648.6 (M+Na$^+$).

c) Compound 4c

A mixture of 2,7-dihydroxy acridine methyl ester, 1c (0.2 g, 0.48 mmol) compound 4b (1.5 g, 2.4 mmol) and cesium carbonate (0.39 g, 1.2 mmol) in anhydrous DMF (10 mL) was heated at 100° C. under a nitrogen atmosphere for 4-5 hours. A small portion of the reaction mixture was then analyzed by HPLC using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=23.5 minutes and was the major component. The reaction was then cooled to room temperature and concentrated under reduced pressure. The residue was partitioned between ethyl acetate (50 mL) and water (50 mL). The ethyl acetate layer was separated, dried over anhydrous magnesium sulfate and concentrated under reduced pressure. The crude product (1.36 g) was purified by flash chromatography on silica gel using 5% methanol in ethyl acetate as eluent. Yield=0.156 g (25%); MALDI-TOF MS 1325 observed.

d) Compound 4e

A mixture of compound 4c (60 mg, 45.3 umoles), distilled 1,3-propane sultone (1.0 g, 8.2 mmol) and sodium bicarbonate (76 mg, 0.9 mmol) was heated at 150° C. under a nitrogen atmosphere. After 2 hours, a small portion was withdrawn, diluted with methanol and analyzed by HPLC using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=17.8 minutes (>80% conversion, starting material Rt=23.5 minutes). The reaction was cooled to room temperature and 20 mL of 1:1, ethyl acetate/hexanes was added. After brief sonication to disperse the gummy product, the solvent was decanted and the product 4d was dried under vacuum.

The crude acridinium ester 4d was suspended in 1 N HCl (10 mL) and refluxed under a nitrogen atmosphere for 2 hours. HPLC analysis, as described above, indicated complete conversion to product 4e eluting at 17 minutes. The product was purified by preparative HPLC using an YMC, $C_{18}$ 30×300 mm column and the same gradient at described above at a solvent flow rate of 20 mL/minute and UV detection at 260 nm. The HPLC fractions containing product were combined and concentrated under reduced pressure. Yield=33.5 mg (52%); MALDI-TOF MS 1433.1 observed.

e) Compound 4f

A solution of compound 4e (33.5 mg, 23.4 umoles) in anhydrous DMF (2 mL) was treated with diisopropylethylamine (6.1 uL, 35 umoles) and TSTU (8.5 mg, 28.2 umoles). The reaction was stirred at room temperature. After 30 minutes, HPLC analysis, as described in section (c) showed complete conversion to the NHS ester eluting at Rt=18.7 minutes. This reaction was added dropwise to a stirred solution of 2,2'-(ethylenedioxy)bis(ethylamine) (35 ul, 0.24 mmol) in anhydrous DMF (1.0 mL). After one hour, HPLC analysis of the reaction mixture, as described in section (c) showed complete conversion to the product 4f eluting at Rt=14.5 minutes. The product was purified by preparative HPLC as described in section (d). Yield=22 mg (59%); MALDI-TOF MS 1565.8 observed.

f) B4-AE-NHS, Compound 4h

A solution of compound 4f (22 mg, 14 umoles) in anhydrous methanol (2 mL) was treated with diisopropylethylamine (12.3 uL, 70 umoles) and glutaric anhydride (8 mg, 70 mmoles). The reaction was stirred at room temperature. After 30 minutes, HPLC analysis, as described in section (d), showed complete conversion to the glutarate derivative 4g eluting at Rt=15.9 minutes. The reaction mixture was diluted with anhydrous toluene (3 mL) and concentrated under reduced pressure.

The crude product was dissolved in anhydrous DMF (2 mL) and treated with diisopropylethylamine (24.6 uL, 0.14 mmol) and TSTU (42 mg, 0.14 mmol). After stirring for 30 minutes, HPLC analysis, as described in section (c), showed >70% conversion to the product 4h eluting at Rt=16.9 minutes. The product was purified by preparative HPLC as described in section (d). The HPLC fractions containing product were frozen at −80° C. and lyophilized to dryness. The lyophilized product was dissolved in anhydrous MeCN and transferred to a tared round bottom flask and concentrated under reduced pressure. Yield=18.8 mg (75%); MALDI-TOF MS 1776.5 observed.

The following reactions describe the synthesis of B4-AE-NHS, 4h.

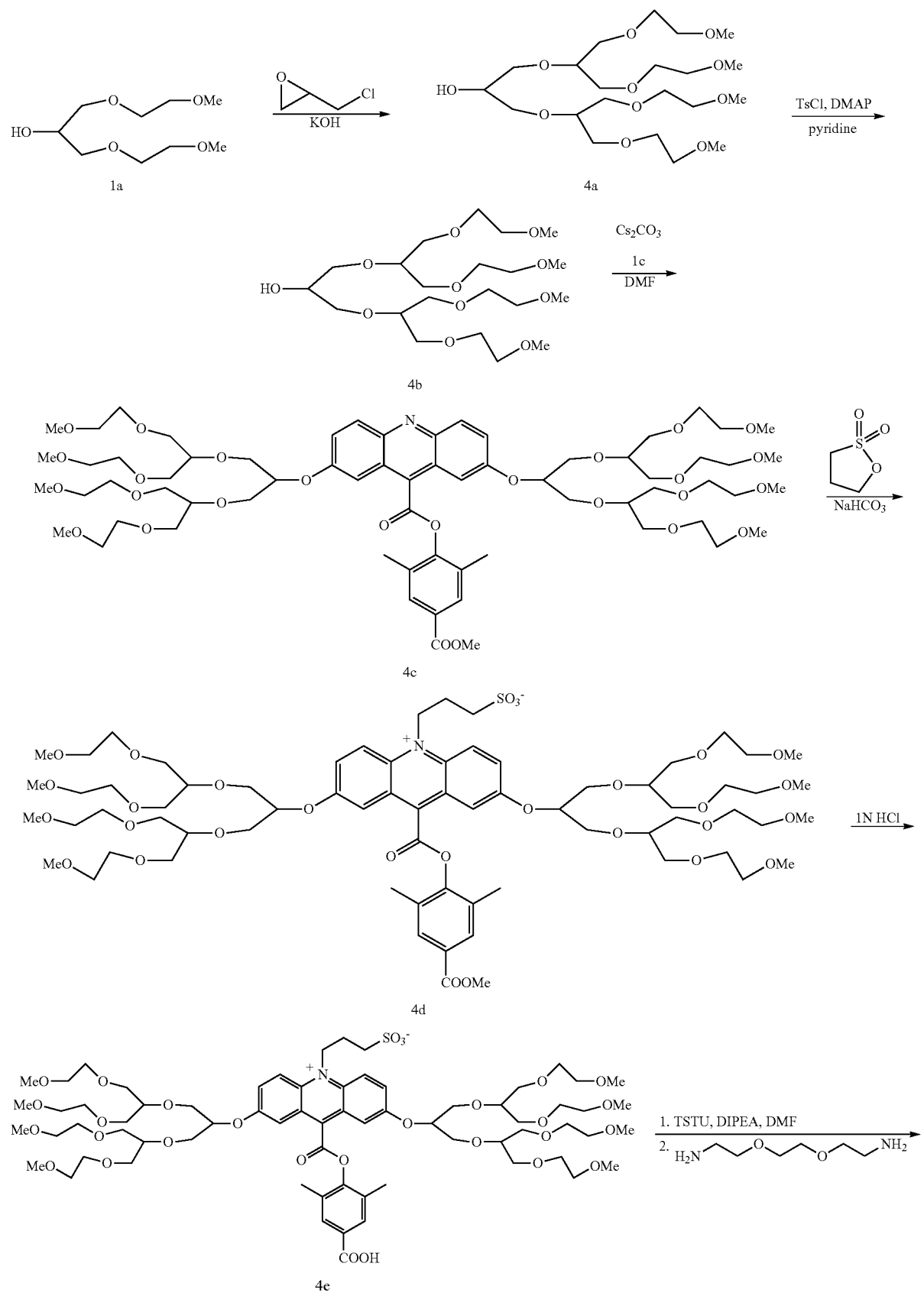

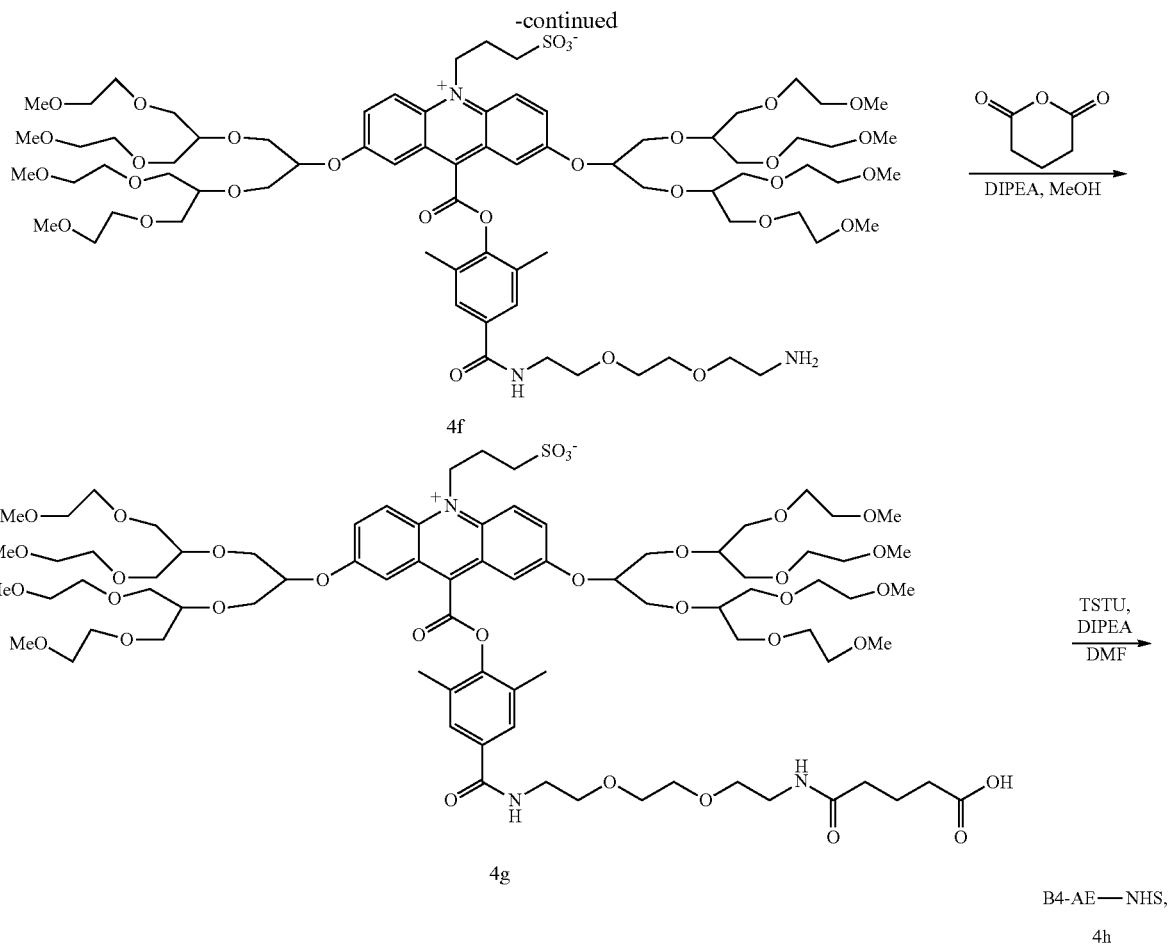

4f

4g

B4-AE—NHS,
4h

Example 5

B04-AE-NHS, 5i a) Compound 5b 1,3-Dimethoxy-2-propanol, 5a, was synthesized as described by Kang et al. in *Bull. Korean Chem. Soc.* 2006, 27, 1364-1370. Crude 1,3-dimethoxy-2-propanol (10.66 g, 0.089 mol) and potassium hydroxide (3 g, 0.00534 mol) was stirred at 80° C. under a nitrogen atmosphere until all the potassium hydroxide dissolved. Epichlorohydrin (1.65 g, 0.00178 mol) was then added dropwise and the reaction was heated at 100° C. under a nitrogen atmosphere for 24 hours. The reaction was then cooled to room temperature and partitioned between ethyl acetate (75 mL) and saturated ammonium chloride solution (75 mL). The ethyl acetate layer was separated and the aqueous layer was extracted once more with ethyl acetate (50 mL). The combined ethyl acetate extracts were dried over anhydrous magnesium sulfate and concentrated under reduced pressure. The recovered light brown oil (3.7 g) was used a such in the next reaction.

b) Compound 5c

Compound 5b (3.7 g, 0.0125 mol) was dissolved an anhydrous pyridine (15 mL) and treated with 4-dimethylpyridine (0.381 g, 3.1 mmol) and p-toluenesulfonyl chloride (4.8 g, 0.0025 mol). The reaction was stirred at room temperature under a nitrogen atmosphere for 3 days. The solvent was then removed under reduced pressure and the residue was partitioned between ethyl acetate (75 mL) and 1N HCl (50 mL). The ethyl acetate layer was separated and washed with 2% sodium hydroxide solution (50 mL) and saturated ammonium chloride solution (50 mL). It was then dried over anhydrous magnesium sulfate and concentrated under reduced pressure. The crude product (6.6 g) was purified by flash chromatography on silica gel using 75:24:1; hexanes:ethyl acetate:methanol as eluent. Yield=1.73 g, light yellow oil.

c) Compound 5d

A mixture of 2,7-dihydroxy acridine methyl ester, 1c (0.1 g, 0.24 mmol) compound 5c (0.54 g, 1.2 mmol) and cesium carbonate (0.2 g, 0.06 mmol) in anhydrous DMF (5 mL) was heated at 100° C. under a nitrogen atmosphere for 4-5 hours. A small portion of the reaction mixture was then analyzed by HPLC using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=26.2 minutes and was the major component. The reaction was then cooled to room temperature and concentrated under reduced pressure. The residue was partitioned between ethyl acetate (75 mL) and water (50 mL). The ethyl acetate layer was separated, dried over anhydrous magnesium sulfate and concentrated under reduced pressure. The crude product (0.45 g) was purified by preparative TLC on silica gel using 1% methanol in ethyl acetate as eluent. Yield=64 g (28%); MALDI-TOF MS 973.8 observed.

d) Compound 5f

A mixture of compound 5d (64 mg, 65.7 umoles), distilled 1,3-propane sultone (1.6 g, 13.1 mmol) and sodium bicarbonate (110 mg, 1.3 mmol) was heated at 150° C. under a nitrogen atmosphere. After 2 hours, a small portion was withdrawn, diluted with methanol and analyzed by HPLC using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm. Product was observed eluting at Rt=20.5 minutes (>60% conversion). The reaction was cooled to room temperature and 20 mL of 1:1, ethyl acetate/hexanes was added. After brief sonication to disperse the gummy product, the solvent was decanted and the product 5e was dried under vacuum.

The crude acridinium ester 5e was suspended in I N HCl (10 mL) and refluxed under a nitrogen atmosphere for 2 hours. HPLC analysis, as described above, indicated complete conversion to product 5f eluting at 17.5 minutes. The product was purified by preparative HPLC using an YMC, $C_{18}$ 30×300 mm column and the same gradient at described above at a solvent flow rate of 20 mL/minute and UV detection at 260 nm. The HPLC fractions containing product were combined and concentrated under reduced pressure. Yield=12 mg (17%); MALDI-TOF MS 1082.4 observed.

e) Compound 5g

A solution of compound 5f (12 mg, 11.1 umoles) in anhydrous DMF (1 mL) was treated with diisopropylethylamine (4.0 uL, 22 umoles) and TSTU (5 mg, 16.7 umoles). The reaction was stirred at room temperature. After 30 minutes, HPLC analysis, as described in section (c) showed complete conversion to the NHS ester eluting at Rt=19.5 minutes. This reaction was added dropwise to a stirred solution of 2,2'-(ethylenedioxy)bis(ethylamine) (16 ul, 0.11 mmol) in anhydrous DMF (1.0 mL). After one hour, HPLC analysis of the reaction mixture, as described in section (c) showed complete conversion to the product 5g eluting at Rt=14.7 minutes. The product was purified by preparative HPLC as described in section (d). Yield=15.4 mg (quantitative); MALDI-TOF MS 1212.9 observed.

f) B04-AE-NHS, Compound 5i

A solution of compound 5g (15.4 mg, 12.7 umoles) in anhydrous methanol (2 mL) was treated with diisopropylethylamine (11 uL, 63.5 umoles) and glutaric anhydride (7.2 mg, 63.5 umoles). The reaction was stirred at room temperature. After 30 minutes, HPLC analysis, as described in section (c), showed complete conversion to the glutarate derivative 5h eluting at Rt=16.2 minutes. The reaction mixture was diluted with anhydrous toluene (3 mL) and concentrated under reduced pressure. The crude product was dissolved in anhydrous DMF (2 mL) and treated with diisopropylethylamine (22 uL, 0.126 mmol) and TSTU (38 mg, 0.126 mmol). After stirring for 15 minutes, HPLC analysis, as described in section (c), showed >80% conversion to the product 5i eluting at Rt=17.2 minutes. The product was purified by preparative HPLC as described in section (d). The HPLC fractions containing product were frozen at –80° C. and lyophilized to dryness. The lyophilized product was dissolved in anhydrous MeCN and transferred to a tared round bottom flask and concentrated under reduced pressure. Yield=12.3 mg (68%); MALDI-TOF MS 1423.8 observed.

The following reactions describe the synthesis of B04-AE-NHS, compound 5i

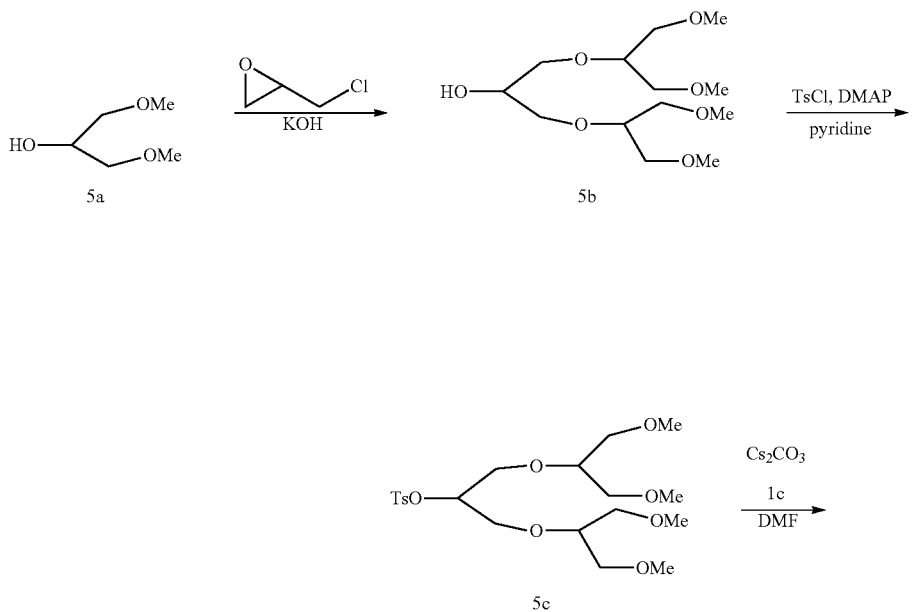

-continued
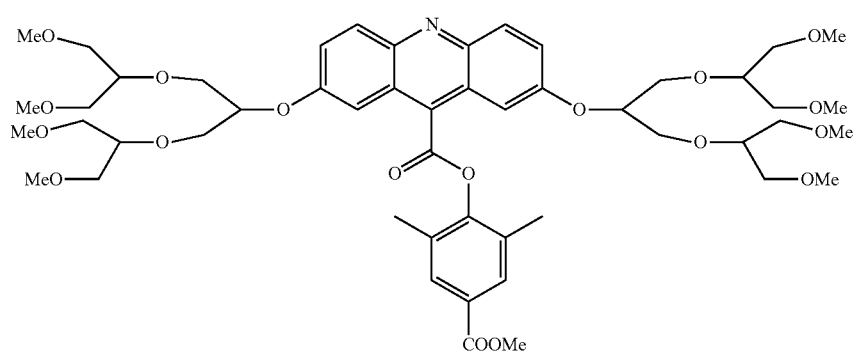
5d
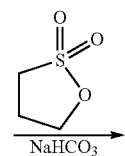
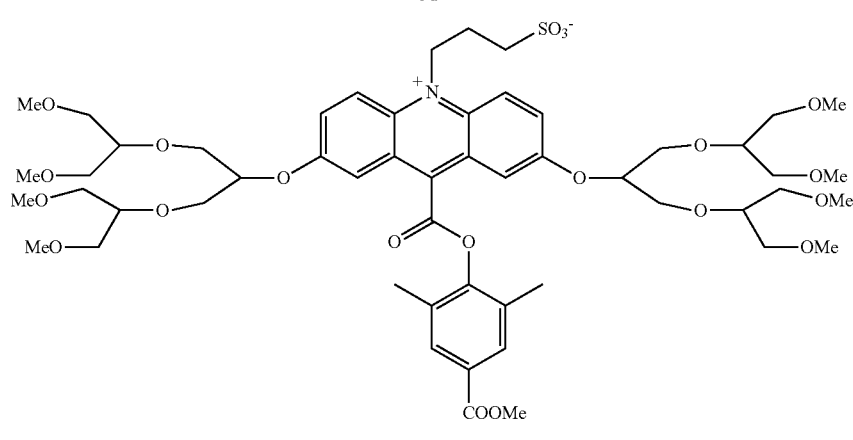
5e
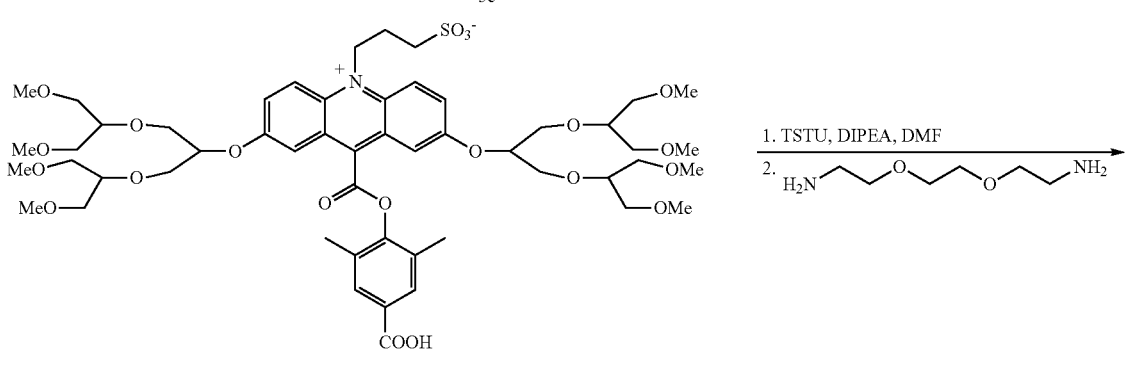
5f
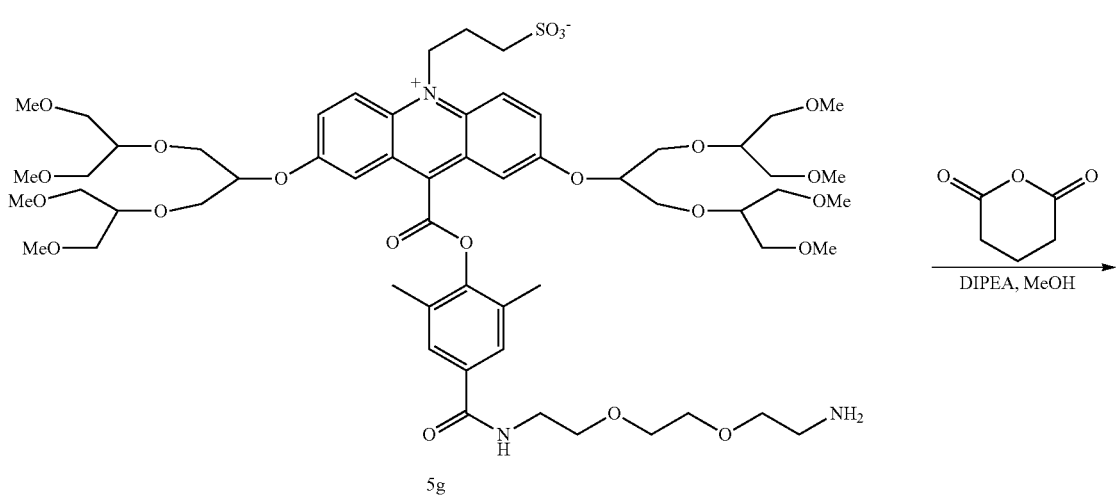
5g

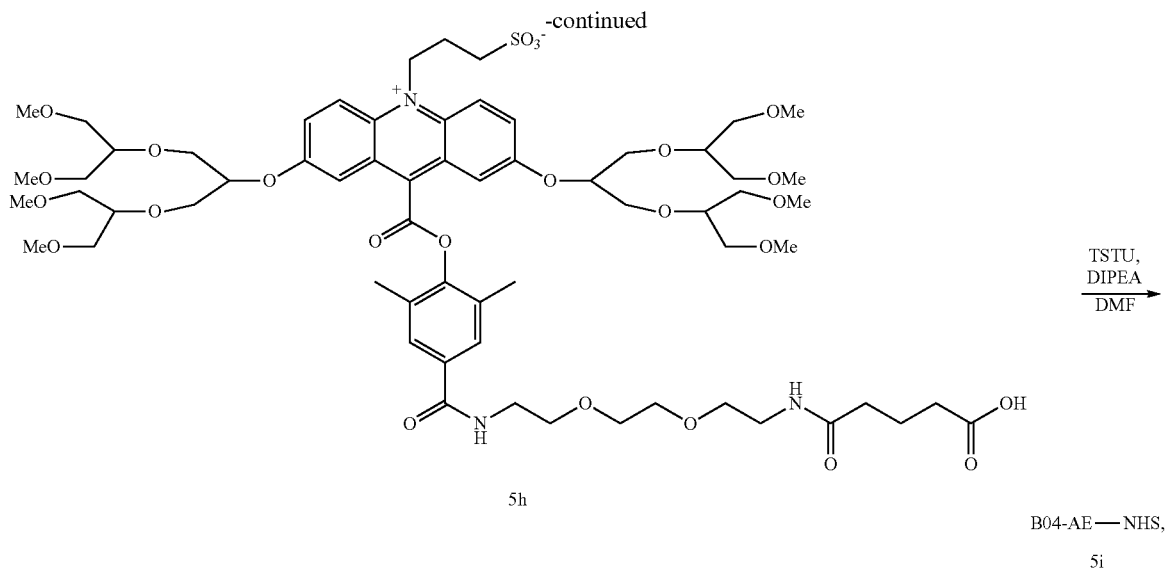

5h

B04-AE—NHS,
5i

Example 6

B1-AE-E2, 6b a) Compound 6a

A solution of compound 1f (26 mg, 28.7 umoles) in anhydrous DMF (2 mL) was treated with diisopropylethylamine (7.5 uL, 43 umoles) and TSTU (10.4 mg, 35 umoles). The reaction was stirred at room temperature. After 30 minutes, HPLC analysis of the reaction mixture using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm, indicated complete conversion to the NHS ester eluting at Rt=18.2 minutes. This reaction was added dropwise to a stirred solution of diamino hexa (ethylene) glycol (U.S. Pat. No. 6,664,043), (40 mg, 0.142 mmol) in anhydrous DMF (2.0 mL). After 30 minutes, HPLC analysis of the reaction mixture showed complete conversion to the product 6a eluting at Rt=14.1 minutes. The product was purified by preparative HPLC using an YMC, $C_{18}$ 30×300 mm column and the same gradient as described above at a solvent flow rate of 20 mL/minute and UV detection at 260 nm. The HPLC fractions containing product were combined and concentrated under reduced pressure. Yield=26 mg (78%); MALDI-TOF MS 1168.6 observed.

b) B1-AE-E2, 6b

Estradiol-6-carboxymethyloxime (1 mg, 2.78 umoles) in DMF (0.1 mL) was combined with compound 6a (3.25 mg, 2.78 umoles) and treated with diisopropylethylamine (1 uL, 5.56 umoles) followed by BOP reagent (1.84 mg, 4.17 umoles) added as a solution in DMF (0.184 mL of a 10 mg/mL solution). The reaction was stirred at room temperature 2h. HPLC analysis, as described in section (a), indicated >80% conversion to the product eluting at Rt=18.2 minutes. The product was purified by preparative HPLC using an YMC, $C_{18}$ 20×250 mm column and a 30 minute of 10→70% B (A=water with 0.05% TFA, B=MeCN with 0.05% TFA) gradient of at a solvent flow rate of 16 mL/minute and UV detection at 260 nm. The HPLC fractions containing product were combined, frozen at −80° C. and lyophilized to dryness. Yield=2.8 mg (67%); MALDI-TOF MS 1511.2 observed.

The following reactions describe the synthesis of B1-AE-E2, 6b.

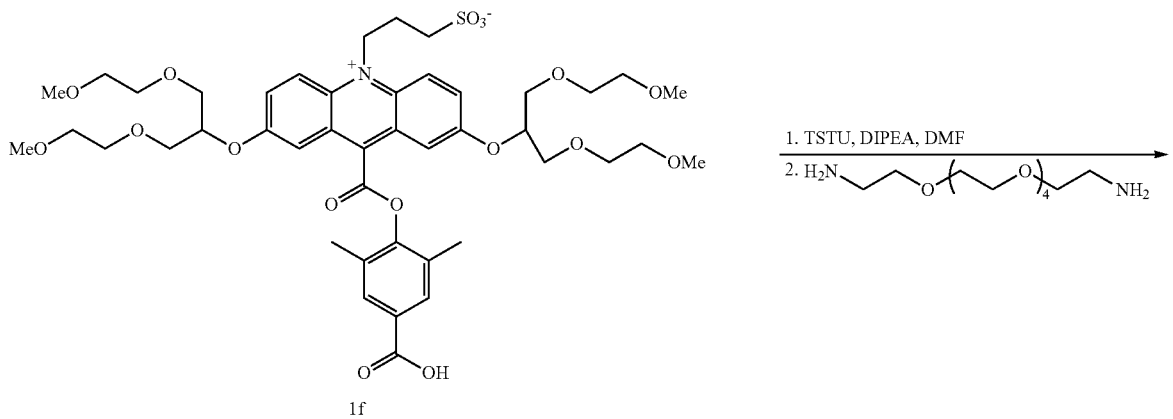

1f

-continued

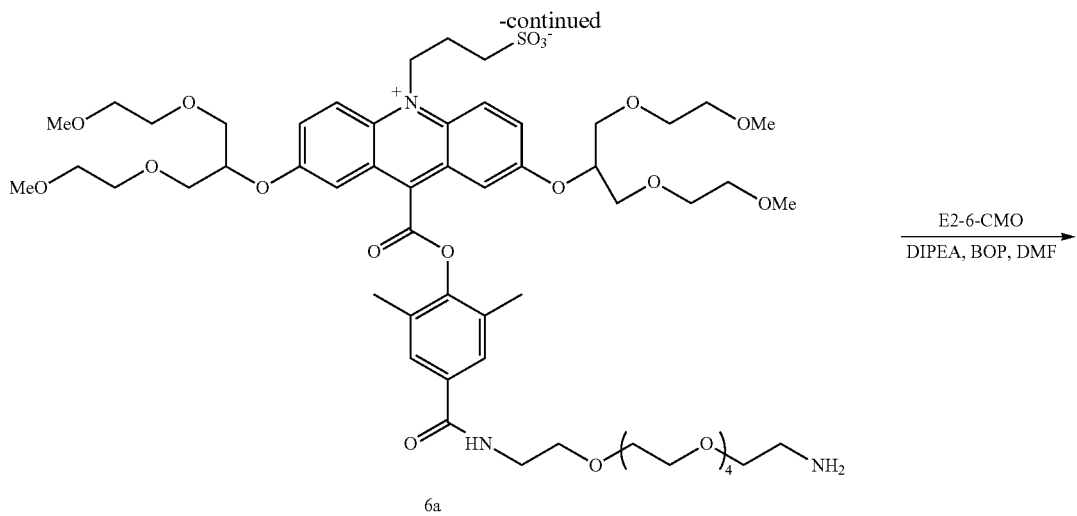

6a

E2-6-CMO
─────────→
DIPEA, BOP, DMF

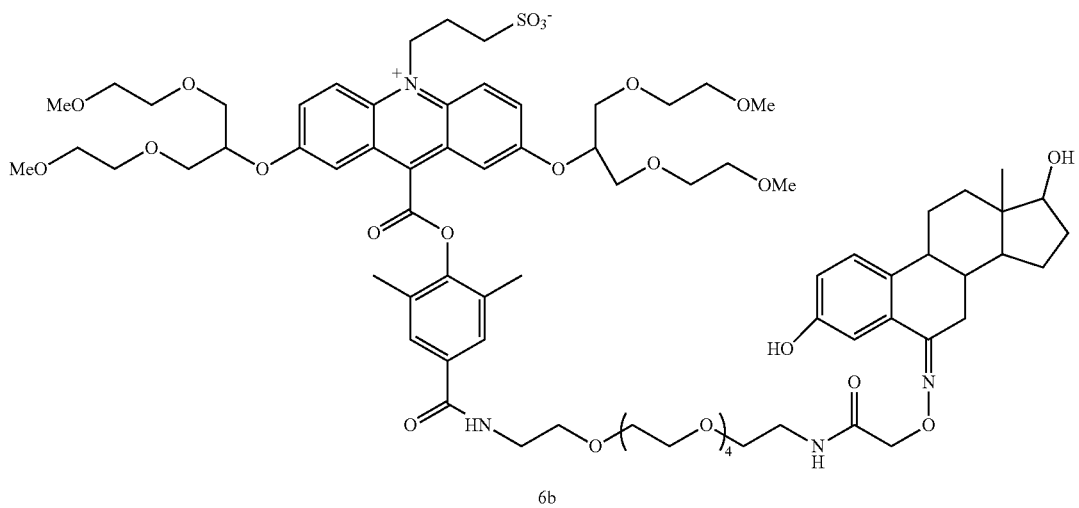

6b

Example 7

B2-AE-E2, 7b a) Compound 7a

A solution of compound 2e (30 mg, 28 umoles) in anhydrous DMF (2 mL) was treated with diisopropylethylamine (7.2 uL, 42 umoles) and TSTU (10 mg, 34 umoles). The reaction was stirred at room temperature. After 30 minutes, HPLC analysis of the reaction mixture using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm, indicated complete conversion to the NHS ester eluting at Rt=17.7 minutes. This reaction was added dropwise to a stirred solution of diamino hexa (ethylene) glycol (U.S. Pat. No. 6,664,043), (40 mg, 0.142 mmol) in anhydrous DMF (1.0 mL). After 30 minutes, HPLC analysis of the reaction mixture showed complete conversion to the product 7a eluting at Rt=14 minutes. The product was purified by preparative HPLC using an YMC, $C_{18}$ 30×300 mm column and the same gradient as described above at a solvent flow rate of 20 mL/minute and UV detection at 260 nm. The HPLC fractions containing product were combined and concentrated under reduced pressure. Yield=28.3 mg (76%); MALDI-TOF MS 1345.4 observed.

b) B2-AE-E2, 7b

Estradiol-6-carboxymethyloxime (1 mg, 2.78 umoles) in DMF (0.1 mL) was combined with compound 7a (3.74 mg, 2.78 umoles) and treated with diisopropylethylamine (1 uL, 5.56 umoles) followed by BOP reagent (1.84 mg, 4.17 umoles) added as a solution in DMF (0.184 mL of a 10 mg/mL solution). The reaction was stirred at room temperature 2h. HPLC analysis, as described in section (a), indicated >80% conversion to the product eluting at Rt=18.1 minutes. The product was purified by preparative HPLC using an YMC, $C_{18}$ 20×250 mm column and a 30 minute of 10→70% B (A=water with 0.05% TFA, B=MeCN with 0.05% TFA) gradient of at a solvent flow rate of 16 mL/minute and UV detection at 260 nm. The HPLC fractions containing product were combined, frozen at −80° C. and lyophilized to dryness. Yield=4.6 mg (98%); MALDI-TOF MS 1688.4 observed.

The following reactions describe the synthesis of B2-AE-E2, 7b.

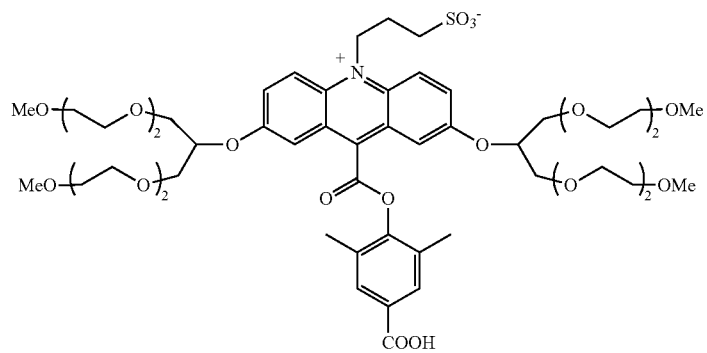

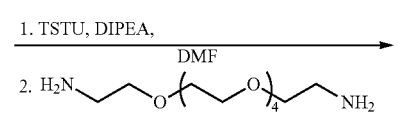

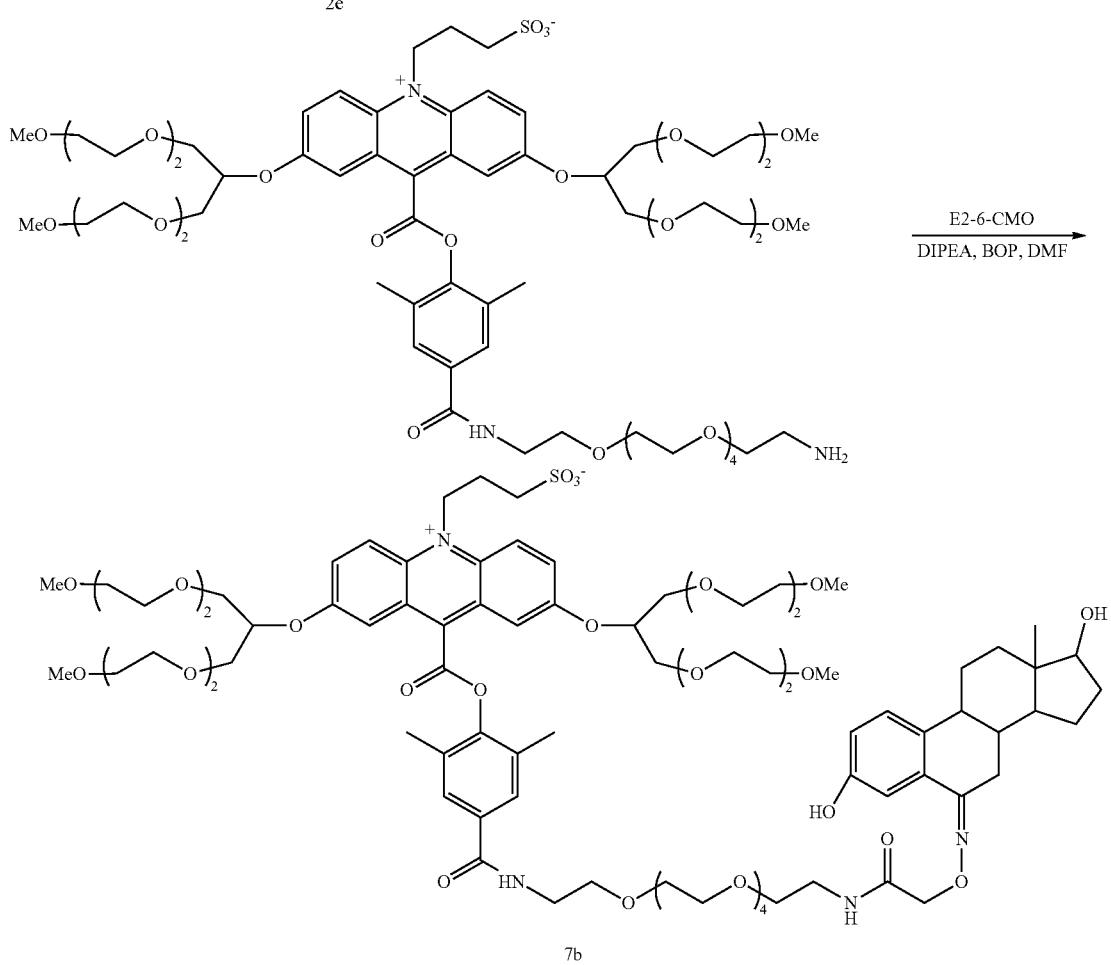

Example 8

B4-AE-E2, 8b a) Compound 8a

A solution of compound 4e (26 mg, 18 umoles) in anhydrous DMF (2 mL) was treated with diisopropylethylamine (4.0 uL, 27 umoles) and TSTU (6.6 mg, 22 umoles). The reaction was stirred at room temperature. After 30 minutes, HPLC analysis of the reaction mixture using a Phenomenex, $C_{18}$ 4.6 mm×25 cm column and a 30 minute gradient of 10→100% B (A=water with 0.05% TFA, B=MeCN with 0.05% TFA) at a flow rate of 1.0 mL/minute and UV detection at 260 nm, indicated complete conversion to the NHS ester eluting at Rt=18.7 minutes. This reaction was added dropwise to a stirred solution of diamino hexa (ethylene) glycol (U.S. Pat. No. 6,664,043), (25 mg, 0.089 mmol) in anhydrous DMF (2.0 mL). After 30 minutes, HPLC analysis of the reaction mixture showed complete conversion to the product 8a eluting at Rt=15.1 minutes. The product was purified by preparative HPLC using an YMC, $C_{18}$ 30×300 mm column and the same gradient as described above at a solvent flow rate of 20 mL/minute and UV detection at 260 nm. The HPLC fractions containing product were combined and concentrated under reduced pressure. Yield=22.5 mg (73%); MALDI-TOF MS 1698.6 observed.

b) B4-AE-E2, 8b

Estradiol-6-carboxymethyloxime (1 mg, 2.78 umoles) in DMF (0.1 mL) was combined with compound 8a (4.72 mg, 2.78 umoles) and treated with diisopropylethylamine (1 uL, 5.56 umoles) followed by BOP reagent (1.84 mg, 4.17 umoles) added as a solution in DMF (0.184 mL of a 10 mg/mL solution). The reaction was stirred at room temperature 2h. HPLC analysis, as described in section (a), indicated >80% conversion to the product eluting at Rt=18.9 minutes. The product was purified by preparative HPLC using an YMC, $C_{18}$ 20×250 mm column and a 30 minute of 10→70% B (A=water with 0.05% TFA, B=MeCN with 0.05% TFA) gradient of at a solvent flow rate of 16 mL/minute and UV detection at 260 nm. The HPLC fractions containing product were combined, frozen at −80° C. and lyophilized to dryness. Yield=4.0 mg (70%); MALDI-TOF MS 2040.9 observed.

The following reactions describe the synthesis of B4-AE-E2, 8b.

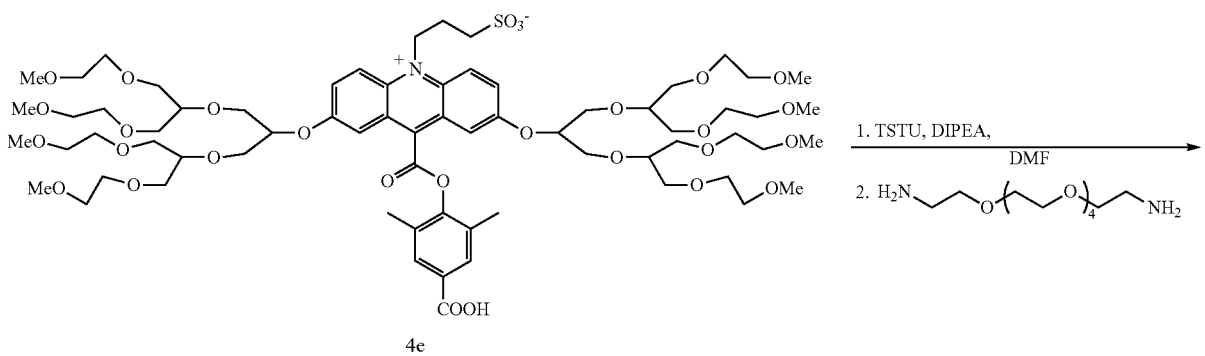

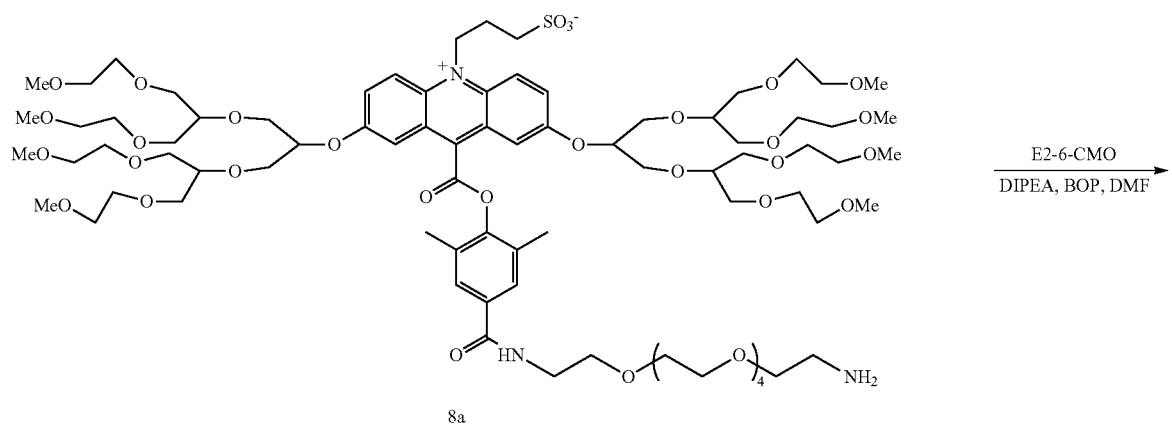

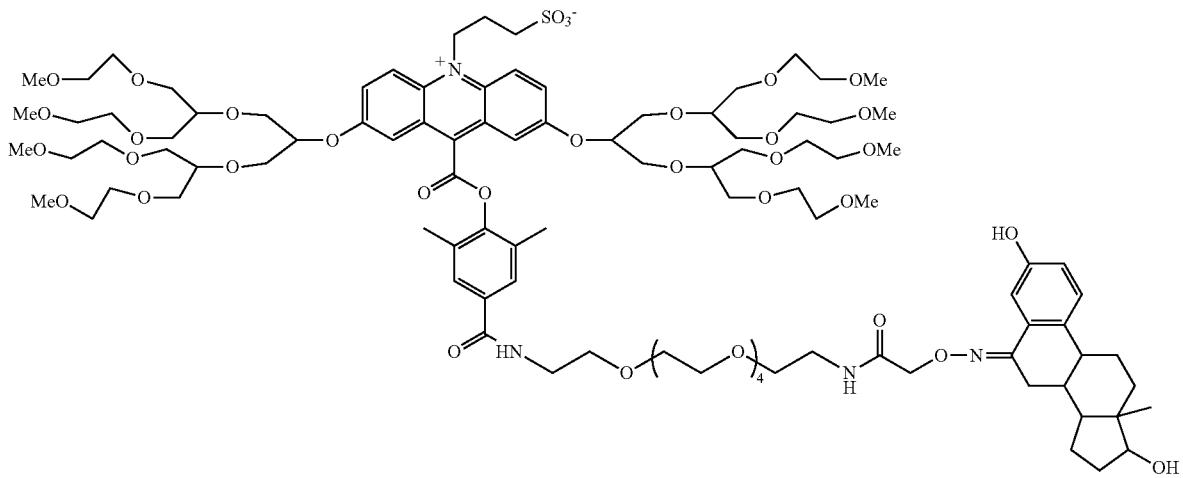

Example 9

General Procedure for Labeling Anti-TSH Mab with Acridinium Ester

A stock solution of the antibody (5 mg/mL, 50 uL, 0.5 mg, 3.4 nmoles) was diluted with either 0.1 M phosphate buffer pH 8 (150 uL) or 0.1 M sodium carbonate pH 9 (150 uL) to give a 2.5 mg/mL solution. To this solution was added 20 equivalents of the acridinium NHS ester as a DMF solution. For example, using B1-AE-NHS, this entailed the addition of 83 ug added as 8.3 uL of a 10 mg/mL DMF solution of the acridinium ester.

The labeling reactions were stirred gently at room temperature for 3-4 hours and were then diluted with de-ionized water (1.8 mL). These diluted solutions were then transferred to 2 mL Centricon™ filters (MW 30,000 cutoff) and centrifuged at 4500G to reduce the volume to ~0.2 mL. This process was repeated three more times. The filtered conjugates were finally diluted into a total volume of 200 uL de-ionized water for mass spectral analysis and RLU measurements.

Mass spectra were recorded on a Voyager DE MALDI-TOF mass spectrometer and the unlabeled antibody was used as the reference. Approximately 2 uL of the conjugate solution was mixed with 2 uL of sinnapinic acid matrix solution (HP) and the spotted on a MALDI plate. After complete drying, mass spectra were recorded. From the difference in mass values for the unlabeled antibody and the conjugates, the extent of AE incorporation could be measured. Typically, under these labeling conditions, 3-6 AE labels were incorporated in the antibody.

Example 10

Measurement of Stability.

Maximization of stability of acridinium esters is one parameter by which assay precision is enhanced. Chemiluminescence stability of several acridinium esters covalently attached to anti-TSH antibody were analyzed for the correlation of molecular structure of the acridinium ester to the stability of chemiluminescent under both a nominal storage temperature of 4° C. and an elevated storage temperature of 37° C. Equivalent amounts of acridinium ester-labeled anti-TSH (thyroid stimulating hormone) antibody each conjugated to a different acridinium ester were diluted to a concentration of 0.2 nanomolar in Siemens Healthcare Diagnostics TSH3 (thyroid stimulating hormone) Lite Reagent buffer consisting of 0.1 M sodium N-(2-hydroxyethyl) piperazine-N'-2-ethanesulfonate (HEPES), 0.15 M sodium chloride, 7.7 mM sodium azide, 1.0 mM tetrasodium ethylenediaminetetraacetate, (EDTA), 12 mM t-octylphenoxypolyethoxyethanol (Triton X-100), 76 uM bovine serum albumin (BSA), 7 uM mouse immunoglobin (IgG), pH 7.7. Each acridinium ester solution was partitioned into two sets of storage vessels. One set of storage vessels was kept at 4° C. and the other at 37° C. Starting from the day of initial dilution the chemiluminescence from 10 microliters of each acridinium ester-antibody solution was determined under standard conditions on a Berthold Technolgies Autolumat LB953 luminometer with sequential addition of 300 microliters each of Siemens Healthcare Diagnostics Flash Reagent 1 (0.1 M nitric acid and 0.5% hydrogen peroxide) and Siemens Healthcare Diagnostics Flash Reagent 2 (0.25 M sodium hydroxide and 0.05% cetyltrimethylammonium chloride).

Example 11

Measurement of Fractional Non-Specific Binding.

Minimization of fractional nonspecific binding (fNSB) of acridinium esters to a solid phase is one parameter by which assay sensitivity is enhanced. The fractional nonspecific bindings of several acridinium esters covalently attached to antiTSH antibody were analyzed for correlation to the molecular structure of the acridinium ester. Equivalent amounts of acridinium ester-labeled antiTSH (thyroid stimulating hormone) antibody each conjugated to a different acridinium ester were diluted to a concentration of 2 nanomolar in Siemens Healthcare Diagnostics TSH3 (thyroid stimulating hormone) Lite Reagent buffer consisting of 0.1 M sodium N-(2-hydroxyethyl) piperazine-N'-2-ethanesulfonate (HEPES), 0.15 M sodium chloride, 7.7 mM sodium azide, 1.0 mM tetrasodium ethylenediaminetetraacetate, (EDTA), 12 mM t-octylphenoxypolyethoxyethanol (Triton X-100), 76 uM bovine serum albumin (BSA), 7 uM mouse immunoglobin (IgG), pH 7.7. Following dilution 100 microliters of the acridinium ester containing solutions were each with 200 microliters of horse serum (Siemens Healthcare Diagnostics Multi-diluent 1) and 200 microliters of either of two solid phases. The first solid phase was 200 microliters of Siemens Healthcare Diagnostics ACS PTH (parathyroid hormone) Solid Phase containing 50 micrograms of magnetic latex microparticles (MLP) derivatized with antiPTH antibody. The second solid phase was 200 microliters of Siemens Healthcare Diagnostics ACS TSH3 (thyroid stimulating hormone) Solid Phase containing 60 micrograms of paramagnetic microparticles (PMP) derivatized with antiTSH antibody. The particles were magnetically collected and washed twice with water after an incubation of 10 minutes to allow interaction between the acridinium ester labeled antibodies and the solid phases. The chemiluminescence of acridinium ester associated with the particles was measured under standard conditions on a Berthold Technolgies Autolumat LB953 luminometer with sequential addition of 300 microliters each of Siemens Healthcare Diagnostics Flash Reagent 1 (0.1 M nitric acid and 0.5% hydrogen peroxide) and Siemens Healthcare Diagnostics Flash Reagent 2 (0.25 M sodium hydroxide and 0.05% cetyltrimethylammonium chloride). Chemiluminescence was measured for 5.0 seconds. Fractional nonspecific binding (fNSB) is calculated as the ratio of particle-bound chemiluminescence to total chemiluminescence input. In general hydrophobicity of an acridinium ester elevates fNSB and is undesirable when distinguishing small amounts of specific signal, conversely hydrophilicity of an acridinium ester lowers fNSB and is desirable when distinguishing small amounts of specific signal.

Example 12

Measurement of Chemiluminescence Kinetics.

Hastening of acridinium ester chemiluminescence rates is one parameter by which assay throughput rates can be increased. Chemiluminescence kinetics of several acridinium esters covalently attached to anti-TSH antibody were analyzed for the correlation of molecular structure of the acridinium ester to its rate of chemiluminescence light emission. Each acridinium ester labeled antibody was diluted to a concentration of 0.2 nanomolar in a buffer consisting of 0.1 M sodium phosphate, 0.15 M sodium chloride, 6 mM sodium azide and 1 g/L bovine serum albumin (BSA). The chemiluminescence kinetics for 10 microliters of each acridinium ester-antibody conjugate tested was integrated in 0.1 second intervals for 20 seconds under standard conditions on a Berthold Technolgies Autolumat LB953 luminometer with sequential addition of 300 microliters each of Siemens Healthcare Diagnostics Flash Reagent 1 (0.1 M nitric acid and 0.5% hydrogen peroxide) and Siemens Healthcare Diagnostics Flash Reagent 2 (0.25 M sodium hydroxide and 0.05% cetyltrimethylammonium chloride). The chemiluminescence kinetics of the tested acridinium esters were compared for relative rate of light emission.

Example 13

Measurement of Quantum Yield.

Increasing acridinium ester chemiluminescence quantum yield is one parameter by which assay sensitivity can be increased. Chemiluminescence quantum yields of several acridinium esters covalently attached to antiTSH antibody were tested for the correlation of molecular structure of the acridinium esters to the magnitude of their chemiluminescence light output. Each acridinium ester labeled antibody was diluted to a concentration of 0.2 nanomolar in a buffer consisting of 0.1 M sodium phosphate, 0.15 M sodium chloride, 6 mM sodium azide and 1 g/L bovine serum albumin (BSA). The chemiluminescence kinetics for 10 microliters of each acridinium ester-antibody conjugate tested was measured for 10 seconds under standard conditions on a Berthold Technolgies Autolumat LB953 luminometer with sequential addition of 300 microliters each of Siemens Healthcare Diagnostics Flash Reagent 1 (0.1 M nitric acid and 0.5% hydrogen peroxide) and Siemens Healthcare Diagnostics Flash Reagent 2 (0.25 M sodium hydroxide and 0.05% cetyltrimethylammonium chloride). The chemiluminescence quantum yield was calculated as the ratio of the chemiluminescence to the amount of acridinium ester tested.

All patent and non-patent literature referenced in this specification is hereby incorporated by reference.

The invention having been described by the foregoing description of the preferred embodiments, it will be understood that the skilled artisan may make modifications and variations of these embodiments without departing from the spirit or scope of the invention as set forth in the following claims.

We claim:

1. An assay for the detection or quantification of an analyte in a sample suspected of containing the analyte comprising the steps of:
   (a) providing a conjugate comprising: (i) a binding molecule specific for the analyte; and (ii) an acridinium ester having the structure:

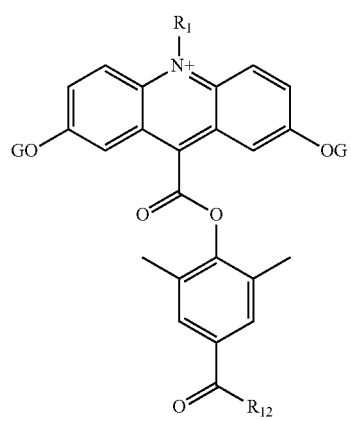

wherein, $R_1$ is a methyl or sulfopropyl group;

G is, at both occurrences, a branched group selected from:

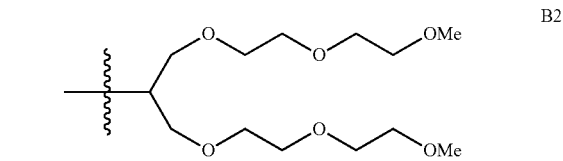

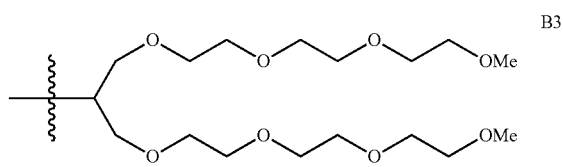

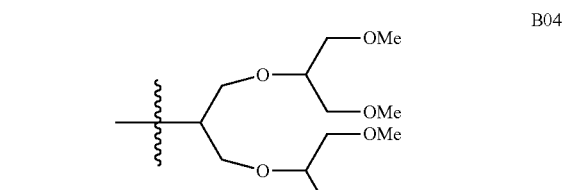

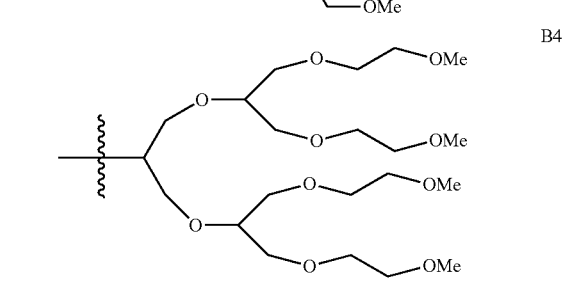

and $R_{12}$ is an electrophilic or nucleophilic group conjugated to the binding molecule specific for the analyte;

(b) providing a solid support having immobilized thereon a second binding molecule specific for the analyte;

(c) mixing the conjugate, the solid phase and the sample suspected of containing the analyte to form a binding complex;

(d) separating the binding complex captured on the solid support;

(e) triggering chemiluminescence of the binding complex from step (d) by adding chemiluminescence triggering reagents;

(f) detecting the presence or calculating the concentration of the analyte by comparing the amount of light emitted from the reaction mixture with a standard dose response curve which relates the amount of light emitted to a known concentration of the analyte.

2. The assay according to claim 1, wherein the conjugate is formed from a conjugate reaction between the binding molecule specific for an analyte and an acridinium ester having the structure:

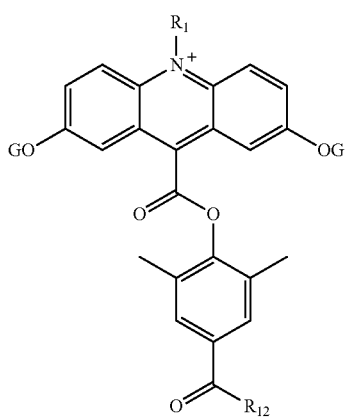

wherein,
R$_{12}$ is an electrophilic or nucleophilic group for conjugating the acridinium ester to the binding molecule.

3. The assay according to claim 2, wherein R$_{12}$ is selected from the group consisting of
(1) OH;
(2) O—N-succinimidyl;
(3) —NH—(CH$_2$)$_5$—C(O)—O—N-succinimidyl;
(4) —NH—(CH$_2$)$_5$—COOH;
(5) —NH—(C$_2$H$_4$O)$_p$—C$_2$H$_4$NH—C(O)—(CH$_2$)$_3$—C(O)—O—N—R'' wherein p=1 to 5; and where R'' is hydrogen or —N— succinimidyl
(6) —NH—(C$_2$H$_4$O)$_q$—C$_2$H$_4$NH$_2$, wherein q=1 to 5; and
(7) —NH—R—NHR, wherein R is independently hydrogen, alkyl, alkenyl, alkynyl, or aralkyl; wherein R optionally comprises up to 20 heteroatoms.

4. The assay according to claim 1, wherein G is a group:

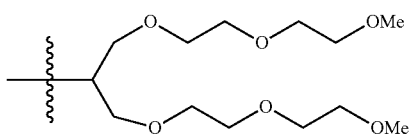

B2 at both occurrences.

5. The assay according to claim 1, wherein G is a group:

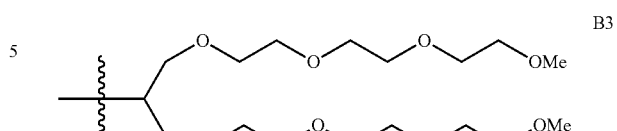

B3 at both occurrences.

6. The assay according to claim 1, wherein G is a group:

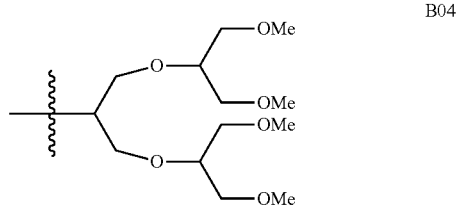 [SMILES: *C(COC(COC)COC)COC(COC)COC]

B04 at both occurrences.

7. The assay according to claim 1, wherein G is a group:

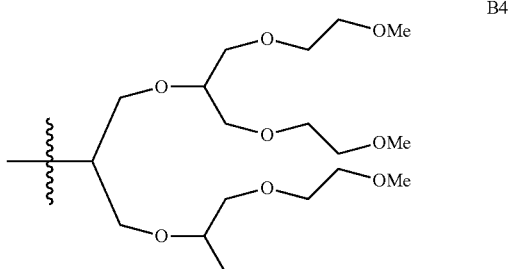

B4 at both occurrences.

8. The assay according to claim 1, wherein said acridinium ester has the structure:

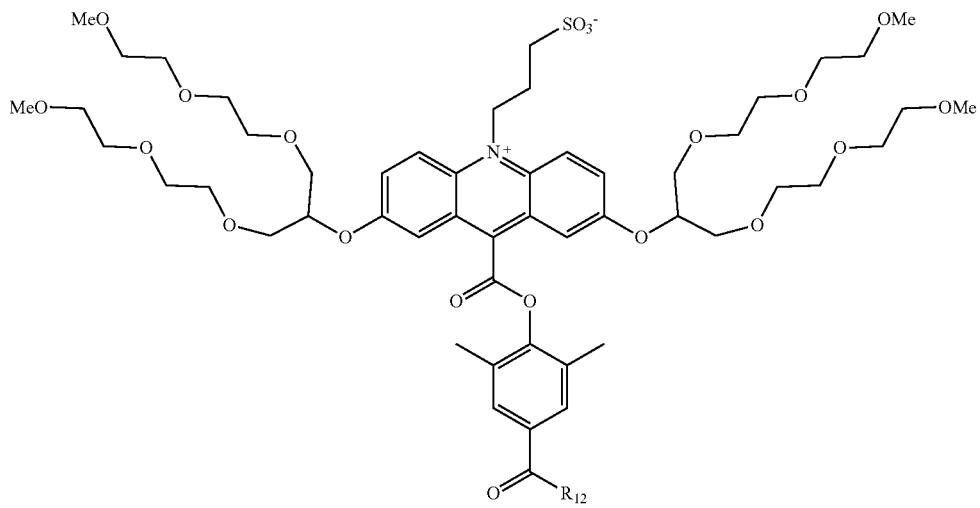

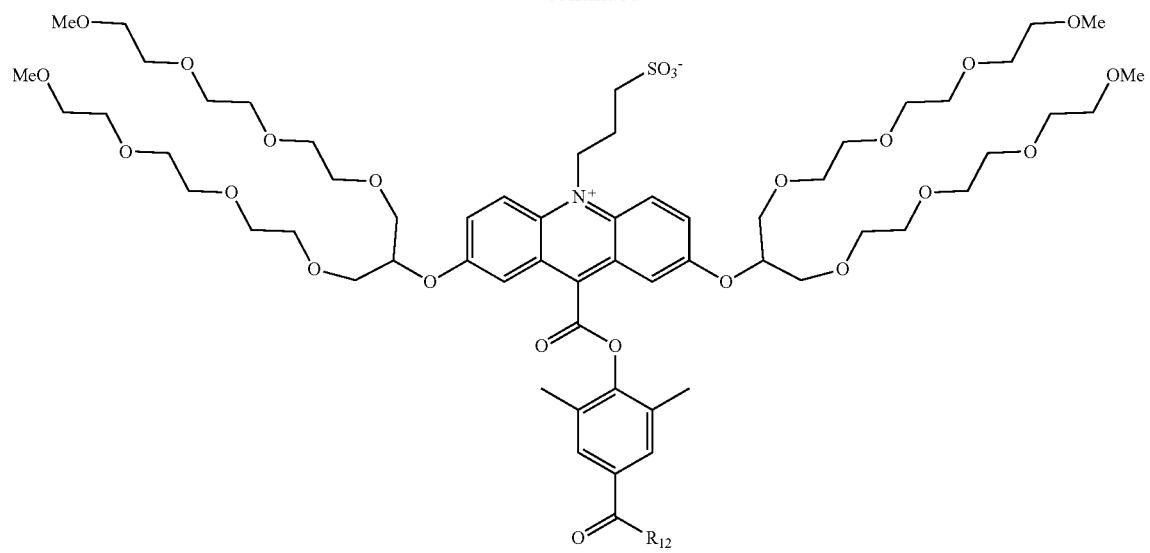
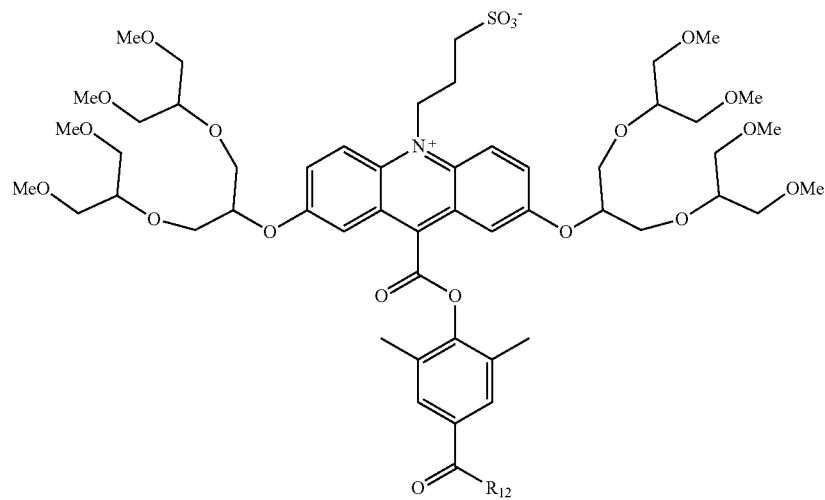
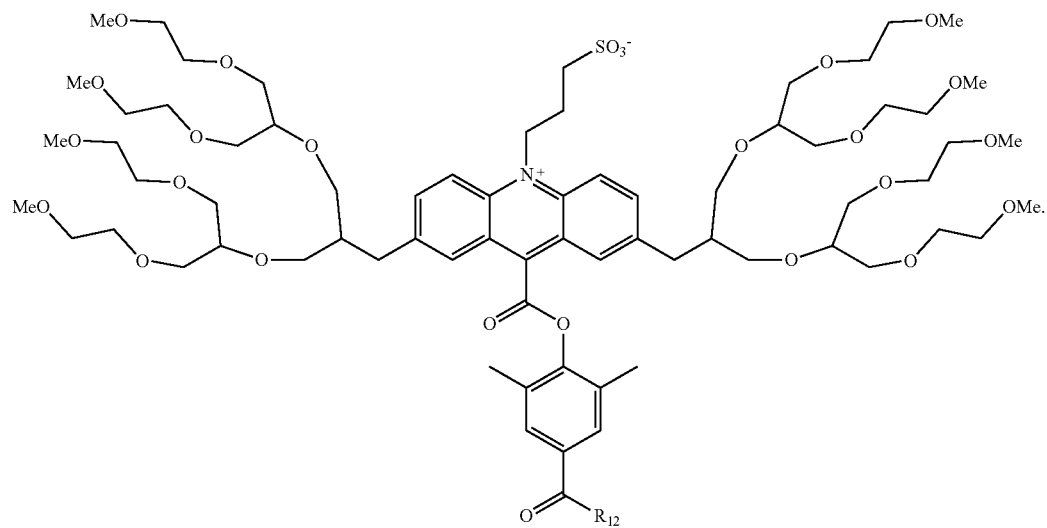

9. The assay according to claim 1, wherein said conjugate is characterized in that ≥89% of the chemiluminescence of said acridinium ester is emitted within one second of said adding chemiluminescence triggering reagents.

10. The assay according to claim 1, wherein said conjugate is characterized in that said conjugate retains more than 60% of its chemiluminescent activity after 33 days at 37° C.

11. The assay according to claim 1, wherein said binding molecule specific for an analyte is an antibody, an antibody fragment, a binding protein, a nucleic acid, a peptide, a receptor, or a synthetic binding molecule.

* * * * *

UNITED STATES PATENT AND TRADEMARK OFFICE
CERTIFICATE OF CORRECTION

PATENT NO. : 11,332,445 B2
APPLICATION NO. : 16/801354
DATED : May 17, 2022
INVENTOR(S) : Anand Natrajan et al.

Page 1 of 2

It is certified that error appears in the above-identified patent and that said Letters Patent is hereby corrected as shown below:

In the Claims

Columns 61-62 (Claim 8):
Please delete the following structure:

"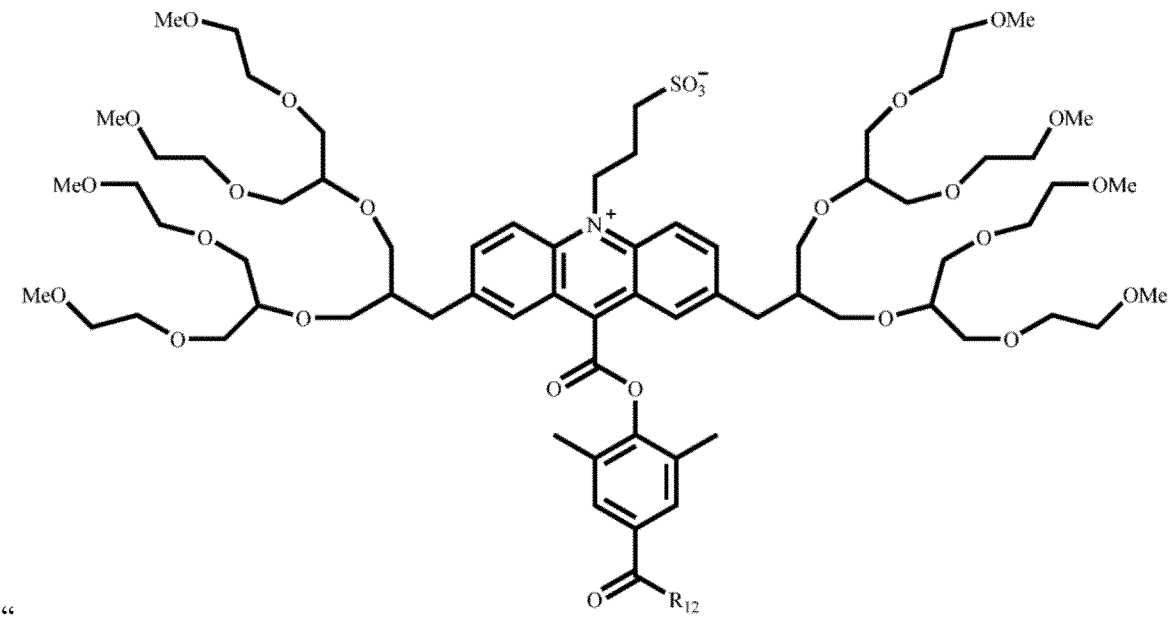"

Signed and Sealed this
Twenty-seventh Day of June, 2023

Katherine Kelly Vidal
*Director of the United States Patent and Trademark Office*

CERTIFICATE OF CORRECTION (continued)
U.S. Pat. No. 11,332,445 B2

And insert the following structure:

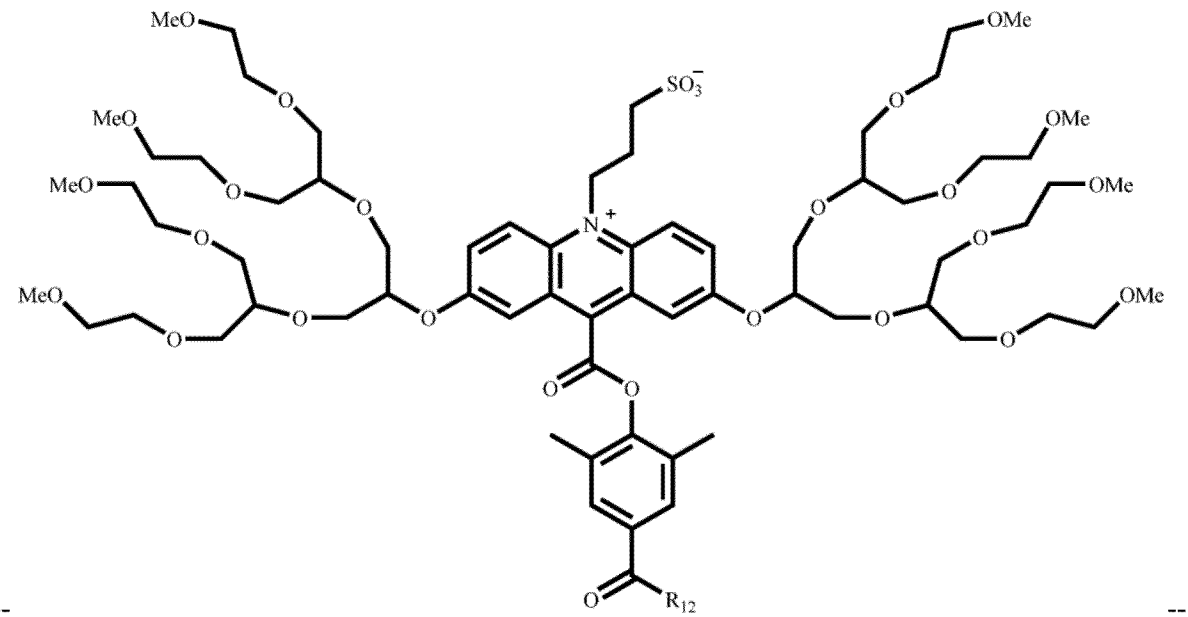

-- --
therefor.